United States Patent
Larsen et al.

(10) Patent No.: US 11,902,730 B2
(45) Date of Patent: Feb. 13, 2024

(54) CUSHION CONFIGURED TO BE SECURED TO AN EAR CUP OF A HEADSET AND/OR HEARING PROTECTION DEVICE

(71) Applicant: INVISIO A/S, Hvidovre (DK)

(72) Inventors: Andreas Bruun Larsen, Copenhagen Ø (DK); Dennis Normann Andersen, Olstykke (DK); Jesper Rye Bønnelykke, Valby (DK); Morten Berg Arnoldus, Frederiksberg C (DK)

(73) Assignee: INVISIO A/S, Hvidovre (DK)

( * ) Notice: Subject to any disclaimer, the term of this patent is extended or adjusted under 35 U.S.C. 154(b) by 26 days.

(21) Appl. No.: 17/423,517

(22) PCT Filed: Jan. 30, 2020

(86) PCT No.: PCT/EP2020/052294
§ 371 (c)(1),
(2) Date: Jul. 16, 2021

(87) PCT Pub. No.: WO2020/157200
PCT Pub. Date: Aug. 6, 2020

(65) Prior Publication Data
US 2022/0124422 A1    Apr. 21, 2022

(30) Foreign Application Priority Data
Jan. 31, 2019 (EP) .................................... 19154750

(51) Int. Cl.
*H04R 25/00* (2006.01)
*H04R 1/10* (2006.01)
*A61F 11/14* (2006.01)

(52) U.S. Cl.
CPC ............ *H04R 1/1008* (2013.01); *A61F 11/14* (2013.01)

(58) Field of Classification Search
CPC .. H04R 1/1058; H04R 1/1008; H04R 1/1066; H04R 1/1075; H04R 1/105
See application file for complete search history.

(56) References Cited

U.S. PATENT DOCUMENTS

| | | | |
|---|---|---|---|
| 4,958,697 A | 9/1990 | Moody | |
| 6,295,366 B1 | 9/2001 | Haller | |
| 9,473,844 B2 * | 10/2016 | Horikawa | ............ H04R 1/1008 |

FOREIGN PATENT DOCUMENTS

| | | |
|---|---|---|
| EP | 2858380 A1 | 4/2015 |
| GB | 1243728 A | 8/1971 |

OTHER PUBLICATIONS

International Search Report and Written Opinion of International Searching Authority for Application No. PCT/EP2020/052294, dated Feb. 24, 2020 (12 pages).

* cited by examiner

*Primary Examiner* — Amir H Etesam
(74) *Attorney, Agent, or Firm* — Ice Miller LLP; Justin D. Swindells

(57) ABSTRACT

A cushion configured to be secured to an ear cup of a headset and/or hearing protection device. The cushion defines an inner opening and includes a contact surface along a periphery proximal part of the cushion. The contact surface is configured to abut against and contact a user's head around an ear of the user when the headset and/or hearing protection device is worn by the user. The contact surface of the cushion has a predetermined height profile where respective height values of the predetermined height profile at multiple locations of the contact surface vary about a center or center point of the cushion. The locations are located nearest or towards the inner opening, and a first height of the predetermined height profile is a globally largest height. The first height is located in an upper front-facing part of the cushion.

30 Claims, 11 Drawing Sheets

CUSHION CONFIGURED TO BE SECURED TO AN EAR CUP OF A HEADSET AND/OR HEARING PROTECTION DEVICE

CROSS-REFERENCE TO RELATED APPLICATIONS

This application is a U.S. National Stage of International Application No. PCT/EP2020/052294, filed Jan. 30, 2020, which claims the benefit of European Patent Application No. 19154750.4, filed Jan. 31, 2019, both of which are incorporated herein by reference in their entireties.

FIELD OF THE INVENTION

The present invention relates generally to a cushion to be secured to an ear cup of a headset and/or hearing protection device increasing noise suppression of ambient sound, i.e. reducing the amount noise entering into an ear cup (when worn by a user) comprising the cushion. More particularly, the present invention relates to a cushion to be secured to an ear cup of a headset and/or hearing protection device, wherein the cushion defines an inner opening and comprises a contact surface along a periphery proximal part of the cushion, the contact surface being configured to abut against and contact a user's head around an ear of the user when the headset and/or hearing protection device is worn by the user. Additionally, the present invention relates to a headset and/or hearing protection device comprising one or two ear cups, where at least one ear cup comprises such a cushion.

BACKGROUND

In relation to over-the-ear headsets and/or hearing protection devices, and in particular for professional use in demanding environments and circumstances e.g. by armed or Special Forces, law enforcement personal, fire fighters, emergency personal, etc., it is, at least for some uses, significant to suppress noise arising from ambient sound, i.e. reducing noise that otherwise would enter into the ear cup(s) of the headset and/or hearing protection device, as much as possible or at least to a certain extent. Noise suppression is important (to varying degrees) for other types of users as well and in principle for all types of uses.

Typical current designs of such headsets or hearing protection devices have ear cups each comprising a cushion of a flexible material to surround and encapsulate an ear of a user wearing the headset/hearing protection device to suppress or at least reduce ambient sound reaching the user's ear. When the user wears the headset/hearing protection device, pressure is typically exerted on the ear cups thereby pressing them against the head of the user and shielding the user's ears from ambient sound. The flexible material of the cushion allows the cushion to fit, at least to an extent, to the individual shape of the user's head. In typical current still most used designs of headsets and/or hearing protection devices, the cushions have a relatively uniformly flat (in the cushion's uncompressed state, i.e. when it is not worn) contact surface at a same equal level for contacting the user's head around the ears.

However, it has been found that such traditional headsets or hearing protection devices still are prone to ambient sound, i.e. ambient noise, entering into the ear cup of a headset or hearing protection device at least in certain situations and especially if the user is relatively physically active and/or operating in demanding environments and circumstances. The presence of ambient sound/noise in the ear cup is, at least in part, influenced by the design of the cushion of the ear cup(s). When a uniformly flat same equal level (in its uncompressed state) cushion is worn it will accommodate to the shape of the head around the ear of a user wearing it to some extent due to comprising a flexible material. However, the cushion will have a varying surface pressure, potentially even with local 'pressure points', due to varying compression of the flexible material arising from the uniformly flat same level shaped cushion abutting against a non-uniform surface of the user's head varying in level, which will reduce or 'weaken' the noise suppression of ambient sound of the cushion. Additionally, the varying surface pressure and/or local 'pressure points' reduces the comfort for the user, especially when wearing a headset or hearing protection device with such cushion(s) for prolonged times of use.

For professional uses e.g. operating in demanding environments and circumstances, ambient noise, even at moderate or low levels, can be associated with serious drawbacks, especially for headsets and/or hearing protection devices comprising radio communication capabilities as it can be crucial to receive orders, directives, objectives, etc. clearly and intelligibly. So even a relatively small improvement in suppression of ambient noise can be quite significant for such professional uses. Additionally, any (big or small) improvement in suppression of ambient noise may offer improved protection against hearing loss, tinnitus, and/or other hearing related hearing impairments.

Even though individual head shapes differ, most people's heads will have a head thickness (in the ear-to-ear direction) that is greater towards the upper part of the head than the thickness towards the lower part of the head. Therefore a headset and/or hearing protection device when worn by a user will tilt the ear cups and thereby the cushions at least to some degree due to the shape of the head. Furthermore, the shape of the head around or in the vicinity of an ear is not a smooth regular surface. For example, under the ear, a recess, indentation, or depression is typically present due to the presence of the upper part of the jaw bone and near the upper part of the ear towards the back of the head there typically also is a recess, indentation, or depression. Likewise a recess, indentation, or depression is typically present near the upper part of the ear towards the front of the head (at or near the temple region). The tilting of the ear cups of the headset and/or hearing protection device (when worn) together with the presence of the above mentioned recesses, indentations, or depressions potentially causes issues in relation to suppression of ambient noise for a headset and/or hearing protection device with a cushion of an ear cup having a relatively flat contact surface. This is due to that openings or gaps may form (i.e. the cushions are not fully or firmly in place against the head of the user) that may increase the level of ambient noise entering inside the cushion of the ear cup, especially when the user is physically active and/or operating in demanding environments and circumstances. Even though certain current cushion designs aims at addressing this, e.g. by having a protrusion or peak at a lower part (under the ear towards the front of the user's face) of the cushion, this has been found to still not be optimal in relation to suppression of ambient noise, especially when the user is physically active and/or operating in demanding environments and circumstances.

Patent application GB 1 243 728 discloses sound attenuation ear cups aimed at closing leakage paths thereby attenuating external sounds to a greater degree than has been attained before. An ear cup is disclosed with a soft, resilient sound-attenuating pad adapted for engagement with a head of a wearer along an area encircling the wearer's ear, the pad having a sealing portion with a sealing surface with a sealing surface for engaging the wearer's head with elliptically annular outer and inner head-engaging flanges spaced apart substantially equidistantly from each other at all points around the periphery of an opening dimensioned to surround the wearer's ear. The sealing portion has a thickness between a rim-engaging base and the sealing surface the outer head-engaging flange that varies around the periphery of the ear cup. The corresponding thickness between the rim-engaging base and the inner head-engaging flange preferably does not vary around the periphery of the ear cup. In one embodiment (e.g. as shown in FIGS. 1-3), starting from the top and proceeding toward the front, the thickness between the rim-engaging base and the sealing surface the outer head-engaging flange at first increases sharply and then decreases gradually in a downward direction along the front of the ear, reaching a minimum at the bottom. Proceeding upwardly along the outer flange behind the ear, the flange thickness increases gradually until it reaches a maximum thickness about two-thirds of the way to the top, and then decreases more rapidly to another minimum at the top. In another embodiment (e.g. as shown in FIGS. 9-11), starting at the top of the outer flange and proceeding toward the front, the thickness of the outer flange increases, gradually, reaching a maximum about two-thirds of the way down the front side of the pad. From there, the flange thickness is substantially constant to the bottom of the pad. Just to the rear of the bottom, there is a pronounced valley in the profile of the pad. From the valley, the thickness of the outer flange increases gradually in an upward direction, reaching a maximum about two-thirds of the way to the top of the pad and then decreases gradually again until the top is reached. However, the disclosed designs are not optimal in relation to noise suppression capabilities of the cushion and/or user comfort, in particular if a user is physically active and/or operating in demanding environments and circumstances, and/or due to tilting of the ear cup when the device is worn by the user.

Patent specification U.S. Pat. No. 6,295,366 discloses an aircraft headset including a pair of ear cups where an ear cup seal of an ear cup having a variable configuration having its thickest region behind and below a wearer's ear, along the wearer's neck, and having its thinnest region adjacent to the front of the wearer's ear along the jaw line. The description of patent specification U.S. Pat. No. 6,295,366 is fully silent about anything of the upper part of the ear cup seal. However, the disclosed design is not optimal in relation to noise suppression capabilities of the cushion and/or user comfort, in particular if a user is physically active and/or operating in demanding environments and circumstances, and/or due to tilting of the ear cup when the device is worn by the user.

Accordingly, it would be an advantage to provide a cushion for an ear cup of a headset and/or a hearing protection device that improves noise suppression of ambient sound (otherwise) entering into an inside of the ear cup, even if a user of the headset and/or a hearing protection device is physically active and/or operating in demanding environments and circumstances, and/or due to tilting of the ear cup when the headset and/or hearing protection device is worn. It would also be an advantage to provide a cushion for an ear cup of a headset and/or a hearing protection device having increased comfort when being worn by a user, even for prolonged periods of use.

SUMMARY

It is an object to provide a cushion configured to be secured to an ear cup of a headset and/or a hearing protection device alleviating one or more of the above mentioned drawbacks at least to an extent, and in particular providing such a cushion with improved noise suppression of ambient sound (i.e. ambient noise) and/or at least maintaining wearing comfort or even increasing it for a number of users (e.g. even for most users).

According to a first aspect, this is achieved, at least to an extent, by a cushion configured to be secured to an ear cup of a device such as a headset and/or hearing protection device. It is to be understood, that the device, the cushion is to be secured to, may function 'only' as a headset in this respect (i.e. without hearing protection), may function only as an active and/or passive hearing protection device (i.e. without headset functionality), or may function as both a headset while also offering active and/or passive hearing protection. The headset and/or hearing protection device may be all types of headsets and/or hearing protection devices comprising at least one cushion; including traditional over the ear or circumaural devices, headsets and/or hearing protection devices having a neckband instead of a headband, helmet mounted headsets and/or hearing protection devices, etc. The cushion defines an inner opening and comprises a contact surface along a periphery proximal part of the cushion. The proximal part of the cushion is a part being closest to the user's head when wearing the headset and/or hearing protection device comprising the cushion. The contact surface is configured to abut against and contact a user's head around an ear of the user when the headset and/or hearing protection device is worn by the user. The contact surface of the cushion has a predetermined height profile where respective height values of the predetermined height profile at a plurality of locations of the contact surface vary about the inner opening of the cushion (and/or a centre or centre point of the cushion), i.e. the plurality of locations of the contact surface (with respective contact surface heights varying about the inner opening and/or centre or centre point) are distributed on the contact surface about the inner opening of the cushion. The contact surface is preferably closed, i.e. goes all the way about the inner opening (and/or centre or centre point) of the cushion. The height values are in the present context relative in the sense that the specific height values are (or may be) given in relation to a predetermined reference height value (or level) of the contact surface. This is opposed e.g. to height values given in relation to an overall (proximal/distal) thickness of the cushion that can be somewhat arbitrary (within certain practical boundaries). The reference height value may e.g. be a lowest height value of the entire cushion's contact surface, i.e. a globally lowest height value. Alternatively, and in particular if the contact surface is radially or transversely sloped (see more in the following), the reference height value may e.g. be a locally lowest height value, e.g. local amongst height values on a same 'track' or radial portion of the contact surface about the inner opening. As examples such different tracks or portions may e.g. be an inner (i.e. closer to the inner opening), innermost, outer (i.e. away from the inner opening), outermost, central, middle, etc. track or portion or in principle also any track or portion between the innermost and the outermost tracks or portions. Alternatively, other respective reference height values may be used. The actual value of the predetermined reference height value(s) is typically not significant but simply provides a common frame of reference for the varying respective heights of the contact surface.

Accordingly, the contact surface is quite irregular and can, at least in some embodiments, vary quite substantially when traversing the contact surface about the inner opening (and/ or the centre or centre point). The centre or centre point will often be located in the inner (e.g. central) opening defined by the cushion. In some embodiments (also referred to herein as radially flat embodiments), the contact surface is a generally flat surface in radial or transverse directions away from or towards the inner opening and/or the centre or centre point of the cushion (while still varying in height about the inner opening as disclosed herein). Such flat or radially flat embodiments may still have a rounding at or near the edges of the contact surface as disclosed herein. In alternative embodiments (also referred to herein as radially sloped embodiments), the contact surface has varying slopes, at least at some locations but e.g. at some or at all locations, in radial or transverse directions away from or towards the inner opening and/or the centre or centre point of the cushion (while additionally varying in height about the centre or centre point as disclosed herein). Accordingly, such radially sloped embodiments thereby have quite varying contact surfaces, varying both about the inner opening (and/or centre or centre point) and radially/transversally.

Additionally according to the first aspect, a first height of the predetermined height profile is a globally largest height of the respective height values at the plurality of locations, where the plurality of locations is located nearest or towards (i.e. at least further towards than a radial or transverse middle of the contact surface of the cushion) and about the inner opening. I.e. the plurality of locations is located about the inner opening traversing the contact surface of the cushion at a part or track of the cushion that is nearest to the inner opening or closer towards the inner opening than a central part or track. The locations could in special cases include the central part or track but more often the locations of the contact surface will be closer or even closest towards the inner opening. See e.g. 410 and 410' in FIGS. 5b and 6a for examples. It is to be understood that the first height may be a global maximum in relation only to height values of the same part or track of the cushion (as specified above), i.e. such a global (in relation to height values of the same part or track) maximum height value may not necessarily be a fully overall global maximum (i.e. a global maximum for all height values of all parts or tracks/the entire contact surface); although it can be. For radially flat embodiments as mentioned herein, the first height will also be an overall global maximum as the height values of the contact surface do not vary radially/transversally. For radially sloped embodiments, the first height may be a global maximum only in relation to the same part or track of the contact surface and not necessarily in relation to height values of all parts/tracks of the contact surface, although it still—in some embodiments—can be an overall global maximum also.

The first height may also be referred to and seen as a peak of the predetermined height profile. For radially or transversely sloped embodiments, inner heights are heights on a part or track of the contact surface being closest or closer towards the inner opening (and/or the centre or centre point), while outer heights are heights on a part or track of the contact surface being furthest or further away from the inner opening (and/or the centre or centre point). In this context, reference to a first height of an inner (or outer) part or track may be made as a first inner (or outer) height. For radially flat embodiments, inner and outer heights (and heights in-between) will generally be the same; this is at least the case for non-rounded contact surfaces. A first (second, third, and/or fourth; see below) height for flat embodiments, may also be referred to as a first (second, third, and/or fourth) flat height. For cushions for an ear pad, it is not uncommon to round the inner and outer edges of the contact surface (see e.g. FIGS. 1-5 and 8-10) to increase user-comfort. For radially flat embodiments, the value of the first (second, third, and/or fourth; see below) height will not change but the area or line of the contact surface having a height value equal to the first height will decrease (in the radial/transverse direction) depending on the rounding angle or amount of rounding being used. A fully rounded contact surface will in principle and ideally speaking only have a single radial/transverse (central) location having a height equal to the first height (whereby the central part or track will also be the inner or innermost part or track). For radially sloped embodiments, rounding the inner and outer edges of the contact surface will generally increase or decrease the height of the inner and outer edges more than for radially flat embodiments and will decrease the first (second, third, and/or fourth; see below) value depending on the rounding angle or amount of rounding. The highest edge (of the inner and outer edge, where which of them being the highest depends on whether the slope is positive or negative) will be reduced. The height of the contact surface of the lowest edge will actually be increased due to the rounding. The contact surface, as used and defined herein, does not include portions of the cushion being rounded (for such rounded embodiments), even though such rounded portions may still contact a user's head at least to some degree when the user is wearing a device comprising a cushion as disclosed herein.

According to the first aspect, the first height is located in an upper front-facing part of the cushion (i.e. towards the upper part and to the front of the head of a user wearing a device comprising the cushion) (see e.g. 102; I: in FIG. 5a). Accordingly, the contact surface at or near the first height will be located at or near a temple region of a user wearing a headset and/or hearing protection device comprising the cushion. This enhances the noise suppression capabilities of the cushion when worn by a user for at least the following reasons. As mentioned, for most users there typically is a recess, indentation, depression, or the like (forth referred to only as recess) present at or near the temple region of the head. The recess together with the overall typical irregular shape of the head (typically being greater in width—in the ear to ear direction—at the top to middle part of the head than the corresponding width of the head towards the jaw and chin) have been found to have a significant impact on the effectiveness of a cushion's ambient noise suppression capabilities, in particular when the user is physically active and/or operating in demanding environments and circumstances. Additionally, many typical cushion designs do not (also) accommodate for the tilting of the cushion (and ear pads) in a sufficient way. By having the (at least inner) globally highest peak (as given by the first height) located as given above then relatively more pressure on the back-facing side of the cushion towards the lower part (but not at the lowest part—somewhere between the middle and lowest part) is applied and the orientation of the cushion is shifted or adjusted accordingly. This together with the 'natural' tilting of the cushion (due to head shape) when worn has surprisingly been found to increase noise suppression. However, it is significant that the peak of the cushion at this location is the (at least inner) globally highest peak of the varying contact surface of the cushion. When wearing such a cushion, the cushion will be put in place around an ear of the user causing the recess of the user's head at or near the temple region and the recess of the user's head below/below and behind the ear to have substantially the same extent or level. Having a cushion accommodating the tilting of the cushion in use in this way also enables a reduction of the overall cushion thickness, at least for a same or corresponding level of noise suppression, which enables reduced weight and thereby increased user comfort. In at least some embodiments, the first height is located at or near the radial 'middle' of the upper front-facing part of the cushion (in quadrant or part I, e.g. at or near about 50°-60°, such as about 55°, about the centre or centre point beginning with 0° at a point between the upper front-facing and the upper back-facing part of the cushion in an anti-clockwise direction), which increases the noise suppression of the cushion even further. Furthermore, user comfort is improved when wearing the cushion due to the height profile varying about the inner opening (and/or the centre or centre point).

In some embodiments, a second height (or at least a second inner height for radially sloped embodiments) of the predetermined height profile is a locally largest height of the respective height values at the plurality of locations, i.e. a local maximum or a locally highest peak (being smaller than the first height; see e.g. 420 and 420' in FIGS. 5b and 6a for examples) where the second height (or the second inner height) is located in a lower back-facing part (see e.g. 104; III: in FIG. 5a) of the cushion. Accordingly, the contact surface at or near the second height/the locally highest peak will be located at or near a recess region of the user's head where the neck is free of the jaw bone of a user wearing a headset and/or hearing protection device comprising the cushion. This recess is generally smaller than the recess near the temple region (where the first height/the globally highest peak of the contact surface is located). This second (smaller) peak has been seen to offer increased noise suppression, and particularly in connection with the first globally highest peak (as given by the first height). In at least some further embodiments, the second height/the locally highest peak is located at or near the radial 'middle' of the lower back-facing part of the cushion (in quadrant or part III, e.g. at or near about 240°-250°, such as about 245°, about the centre or centre point beginning with 0° at a point between the upper front-facing and the upper back-facing part of the cushion in an anti-clockwise direction), which increases the noise suppression of the cushion even further, i.e. the second height/the locally highest peak is, at least in this embodiment, not located at the lower part of cushion but higher up. For (at least some) radially sloped embodiments, the second (outer) height is an overall globally largest height, i.e. an overall global maximum or a global highest peak (see e.g. 420" in FIG. 6b for an example) thereby being larger than the first outer height (whereby the first outer height then still is a locally largest outer height). This still enhance the noise suppression capabilities of the cushion. Furthermore, this will typically improve user comfort when wearing the cushion (when compared to radially/transversally flat embodiments and even more so when compared to traditional cushions without varying heights about the inner opening and/or the centre or centre point). The first and second heights may also be equal or be substantially equal (both for flat and for radially sloped embodiments). This will still increase noise suppression but may reduce user comfort somewhat (but will still improve user comfort over traditional cushions being fully flat, without varying heights about the inner opening and/or the centre or centre point).

In some embodiments, a third (flat, inner, and/or outer) height of the predetermined height profile is a globally smallest height of the respective height values, i.e. a global minimum or a globally lowest valley (see e.g. 430, 430' and 430" in FIGS. 5b, 6a, and 6b for examples), where the third height is located in a lower part (see e.g. 103, II: and 104, III: in FIG. 5a) of the cushion. Accordingly, the contact surface at or near the third height/the globally lowest valley will be located at or near an upper part of the jaw bone of a user wearing a headset and/or hearing protection device comprising the cushion. The further provision of third height/the global lowest valley has been seen to offer further increased noise suppression, in particular in connection with the first height/globally highest peak and even further in connection with both the first height/globally highest peak and the second height/the locally highest peak. In preferred further embodiments, the third (flat or inner) height/global lowest valley is located in a lower front-facing part (see e.g. 103, II: in FIG. 5a) of the cushion. In at least some further embodiments, the third height/global lowest valley is located at or near the 'middle' of the lower front-facing part of the cushion (in quadrant or part II, e.g. at or near about 150°-160°, such as about 155°, about the centre or centre point beginning with 0° at a point between the upper front-facing and the upper back-facing part of the cushion in an anti-clockwise direction), which increases the noise suppression of the cushion even further. In other preferred embodiments for radially sloped embodiments, the third (outer) height/global lowest valley is located in a lower back-facing part (see e.g. 104, III: in FIG. 5a) of the cushion.

In some embodiments, a fourth (flat, inner, and/or outer) height of the predetermined height profile is a locally smallest height of the respective height values, i.e. a local minimum or a locally lowest valley, where the fourth height (see e.g. 440, 440', 440" in FIGS. 5b, 6a, and 6b) is located in a back-facing part (see e.g. 104, III: and 105, IV: in FIG. 5a) of the cushion. The locally lowest valley associated with the fourth height is not as 'deep' as the global minimum or a global lowest valley associated with the third height.

In preferred further embodiments, the fourth height/locally lowest valley is located in an upper back-facing part (see e.g. 105, IV: in FIG. 5a) of the cushion. The additional provision of the fourth height/the locally lowest valley increases noise suppression further, and particularly in connection with the first height/globally highest peak and even further in further connection with the second height/the locally highest peak and/or the third height/the globally lowest valley. In at least some further embodiments, the fourth height/locally lowest valley is located at or near the 'middle' of the upper back-facing part of the cushion (in quadrant or part IV, e.g. at or near about 330°-340°, such as about 335°, about the centre or centre point beginning with 0° at a point between the upper front-facing and the upper back-facing part of the cushion in an anti-clockwise direction), which increases the noise suppression of the cushion even further.

In some further embodiments, the respective height values of the predetermined height profile (flat and inner and outer values as well as values in-between) in the upper back-facing part include at least a non-monotonic segment. This enables the cushion to more accurately follow a typical or average shape of the head (even when the cushion is tilted) of a user in this area of the head, which typically varies more. This increases user comfort and—together with at least the first height/the globally highest peak and optionally in addition with one or more the other peaks and valleys associated with the second to fourth heights mentioned above—increases the noise suppression capabilities of the cushion. In at least some embodiments, the upper back-facing part comprises a (flat or inner) small peak (which could be defined by at least a fifth height) being adjacent to the fourth height/the locally lowest valley. The (flat and inner) small peak may e.g. be closer to the lower back-facing part (see e.g. 104, III: in FIG. 5a) than the fourth height/the locally lowest valley. In at least some further embodiments, the fifth height is located in the upper back-facing part of the cushion (in quadrant or part IV, e.g. at or near about 290°-305°, such as about 300°, about the centre or centre point beginning with 0° at a point between the upper front-facing and the upper back-facing part of the cushion in an anti-clockwise direction), which increases the noise suppression of the cushion even further. In alternative embodiments, the heights of the upper back-facing part do not vary. This simplifies manufacturing of the cushion but this part will not follow the shape a user's head as closely potentially at some (relatively) small detriment to the noise suppression capabilities and/or user comfort of the cushion.

As mentioned, in at least some embodiments, the contact surface is a generally flat surface in radial or transverse directions (also simply referred to radial direction herein) away from or towards the inner opening and/or the centre or centre point of the cushion. This makes the cushion simpler to manufacture while still providing increased noise suppression and/or some increase in user comfort due to the varying heights of the contact surface; especially when compared to traditional cushions with a fully flat contact surface. Also as mentioned, in alternative embodiments, the contact surface has varying slopes, at least at some locations but e.g. at some or at all locations, in radial or transverse directions away from the centre or centre point of the cushion. The radially/transversely sloped contact surface enables an even closer fit to a user's head shape (thereby increasing user comfort further) and even further increased noise suppression (due to the closer fit). The radial/transverse slope may be linear or alternatively non-linear.

In at least some embodiments, a first (flat, inner, and/or outer) difference in height (see e.g. d1, d1', or d1" in FIGS. 5b, 6a, and 6b) between the first (flat, inner, and/or outer) height and the third (flat, inner, and/or outer) height may be defined.

In some embodiments, a second (flat, inner, and/or outer) difference in height (see e.g. d2, d2', or d2" in FIGS. 5b, 6a, and 6b) between the second (flat, inner, and/or outer) height and the third (flat, inner, and/or outer) height may be defined, where the second (flat or inner) difference in height (d2, d2') is smaller than the first (flat or inner) difference in height (d1, d1').

In some embodiments, a third (flat, inner, and/or outer) difference in height (see e.g. d3, d3', or d3" in FIGS. 5b, 6a, and 6b) between the fourth (flat, inner, and/or outer) height and the third (flat, inner, and/or outer) height may be defined, where the third (flat, inner, and/or outer) difference in height (d3, d3', d3") is smaller than the first (flat, inner, and/or outer) difference in height (d1, d1', d1"), and, if the cushion comprises a second (flat, inner, and/or outer) height/locally highest peak, the third (flat, inner, and/or outer) difference in height (d3, d3', d3") is also smaller than the second (flat, inner, and/or outer) difference in height (d2, d2', d3").

In some embodiments, the first (flat) difference in height (d1) is about 4 millimetres to about 10 millimetres, or more preferably about 6 millimetres to about 8 millimetres, e.g. about 7 millimetres.

In some embodiments, the second (flat) difference in height (d2) is about 3 millimetres to about 9 millimetres, or more preferably about 5 millimetres to about 7 millimetres, e.g. about 6 millimetres.

In some embodiments, the third (flat) difference in height (d3) is about 1 millimetres to about 6 millimetres, or more preferably about 2 millimetres to about 4 millimetres, e.g. about 3 millimetres.

In some embodiments, the second (flat) difference in height (d2) is about 70% to about 90%, or more preferably about 75% to about 85%, or even more preferably about 78% to about 82% of the first difference in height (d1), e.g. about 80% of the first difference in height (d1).

In some embodiments, the third (flat) difference in height (d3) is about 35% to about 60%, or more preferably about 40% to about 55%, or even more preferably about 45% to about 49% of the first difference in height (d1), e.g. about 47% of the first difference in height (d1).

As mentioned, in some embodiments, the contact surface has varying slopes, at least at one or some locations but e.g. all locations, in radial or transverse directions away from or towards the inner opening and/or the centre or centre point of the cushion.

As mentioned, an inner height is a respective height at an inner edge of the contact surface closest or closer to the inner opening and/or the centre or centre point, while an outer height is a respective height at an outer edge of the contact surface furthest or further away from the inner opening and/or the centre or centre point.

In some embodiments, the predetermined height profile comprises a first inner height and a first outer height and where a third inner height of the predetermined height profile is a globally smallest inner height of the respective height values and where a third outer height of the predetermined height profile is a globally smallest outer height of the respective height values, where the third inner and outer heights are located in a lower part of the cushion, e.g. (for inner) in a lower front-facing part of the cushion or (for outer) in a lower back-facing part.

In the following, exemplary height values are given for non-rounded and rounded embodiments. The given height values are given, as mentioned, in relation to a minimum value for a same track or radial portion of the contact surface, i.e. an inner height value is given relative to an inner minimum height value and an outer height value is given relative to an outer minimum height value. Alternatively, the height values could be given relative to one single overall global minimum height value; this would just adjust the values to be different but still give the same height variations.

In some (non-rounded) embodiments,
a first inner difference in height (d1') between the first inner height and the third inner height is about 3 millimetres to about 8 millimetres, more preferably about 4 millimetres to about 7 millimetres, e.g. about 6 millimetres, and/or
a first outer difference in height (d1") between the first outer height and the third outer height is about 7 millimetres to about 12 millimetres, more preferably about 8 millimetres to about 10 millimetres, e.g. about 9 millimetres.

In some (rounded) embodiments, the first inner difference in height (d1') is about 5 millimetres to about 10 millimetres, more preferably about 6 millimetres to about 9 millimetres, e.g. about 7 millimetres, and/or the first outer difference in height (d1") between the first outer height and the third outer height is about 6 millimetres to about 11 millimetres, more preferably about 7 millimetres to about 10 millimetres, e.g. about 9 millimetres.

In some (non-rounded or rounded) embodiments,
a second inner height of the predetermined height profile is a locally largest inner height of the respective height values, where the second inner height is located in a lower back-facing part of the cushion, and a second outer height of the predetermined height profile is a locally largest outer height of the respective height values or a globally largest outer height of the respective height values, where the second outer height is located in a lower back-facing part.

In some (non-rounded) embodiments,
- a second inner difference in height (d2') between the second inner height and the third inner height is about 2 millimetres to about 7 millimetres, more preferably about 3 millimetres to about 6 millimetres, e.g. about 4 millimetres, and/or
- a second outer difference in height (d2") between the second outer height and the third outer height is about 7 millimetres to about 11 millimetres, more preferably about 8 millimetres to about 10 millimetres, e.g. about 9 millimetres, and wherein the second inner difference in height (d2') is smaller than the first inner difference in height (d1') and the second outer difference in height (d2") is larger than the first outer difference in height (d1").

In some (rounded) embodiments, the second inner difference in height (d2') between the second inner height and the third inner height is about 4 millimetres to about 8 millimetres, more preferably about 5 millimetres to about 7 millimetres, e.g. about 6 millimetres, and/or the second outer difference in height (d2") between the second outer height and the third outer height is about 7 millimetres to about 11 millimetres, more preferably about 8 millimetres to about 10 millimetres, e.g. about 9 millimetres, and wherein the second inner difference in height (d2') is smaller than the first inner difference in height (d1') and the second outer difference in height (d2") is larger than the first outer difference in height (d1").

In some embodiments, a fourth inner height of the predetermined height profile is a locally smallest inner height of the respective height values, and a fourth outer height of the predetermined height profile is a locally smallest outer height of the respective height values, and where the fourth inner and outer heights are located in a back-facing part of the cushion, e.g. in an upper back-facing part (see e.g. 105, IV: in FIG. 5a) of the cushion.

In some (non-rounded) embodiments,
- a third inner difference in height (d3') between the fourth inner height and the third inner height is about 1 millimetres to about 5 millimetres, or more preferably about 2 millimetres to about 4 millimetres, e.g. about 3 millimetres, and/or
- a third outer difference in height (d3") between the fourth outer height and the third outer height is about 2 millimetres to about 6 millimetres, or more preferably about 3 millimetres to about 5 millimetres, e.g. about 4 millimetres, and wherein the third inner difference in height (d3') is smaller than the first inner difference in height (d1'), and/or wherein the third outer difference in height (d3") is smaller than the first outer difference in height (d1"), and if the cushion comprises a second height, the third inner difference in height (d3') is smaller than the second inner difference in height (d2') and/or the third outer difference in height (d3") is smaller than the second outer difference in height (d2").

In some (rounded) embodiments, the third inner difference in height (d3') between the fourth inner height and the third inner height is about 1 millimetres to about 6 millimetres, or more preferably about 2 millimetres to about 5 millimetres, e.g. about 3 millimetres, and/or the third outer difference in height (d3") between the fourth outer height and the third outer height is about 2 millimetres to about 6 millimetres, or more preferably about 3 millimetres to about 5 millimetres, e.g. about 4 millimetres, and wherein the third inner difference in height (d3') is smaller than the first inner difference in height (d1'), and/or wherein the third outer difference in height (d3") is smaller than the first outer difference in height (d1"), and if the cushion comprises a second height, the third inner difference in height (d3') is smaller than the second inner difference in height (d2') and/or the third outer difference in height (d3") is smaller than the second outer difference in height (d2").

In some (non-rounded) embodiments,
- a second inner difference in height (d2') between the second inner height and the third inner height is about 75% to about 95%, or more preferably about 80% to about 90%, or even more preferably about 75% to about 85%, e.g. about 80%, of a first inner difference in height (d1') between the first inner height and the third inner height, and/or
- wherein a third inner difference in height (d3') between the fourth inner height and the third inner height is about 35% to about 65%, or more preferably about 40% to about 60%, or even more preferably about 45% to about 55%, e.g. about 50%, of a first inner difference in height (d1') between the first inner height and the third inner height.

In some (rounded) embodiments,
- a second inner difference in height (d2') between the second inner height and the third inner height is about 75% to about 97%, or more preferably about 80% to about 95, or even more preferably about 85% to about 90%, e.g. about 87%, of a first inner difference in height (d1') between the first inner height and the third inner height, and/or
- wherein a third inner difference in height (d3') between the fourth inner height and the third inner height is about 30% to about 60%, or more preferably about 35% to about 55%, or even more preferably about 40% to about 50%, e.g. about 46%, of a first inner difference in height (d1') between the first inner height and the third inner height.

In some (non-rounded) embodiments,
- a second outer difference in height (d2") between the second outer height and the third outer height is about 100% to about 115%, or more preferably about 105% to about 110%, e.g. about 107%, of a first outer difference in height (d1") between the first outer height and the third outer height, and/or
- wherein a third outer difference in height (d3") between the fourth outer height and the third outer height is about 35% to about 60%, or more preferably about 40% to about 55%, or even more preferably about 45% to about 50%, e.g. about 47%, of a first outer difference in height (d1") between the first outer height and the third outer height.

In some (rounded) embodiments,
- a second outer difference in height (d2") between the second outer height (420") and the third outer height (430") is about 90% to about 110%, or more preferably about 95% to about 105%, e.g. about 101%, of a first outer difference in height (d1") between the first outer height (410") and the third outer height, and/or
- wherein a third outer difference in height (d3") between the fourth outer height and the third outer height is about 35% to about 60%, or more preferably about 40% to about 55%, or even more preferably about 45% to about 50%, e.g. about 48%, of a first outer difference in height (d1") between the first outer height and the third outer height.

These specific height variations about the centre or centre point are not large however it has been seen to have a significant impact on improving noise suppression and furthermore at least maintaining wearing comfort and for many users even increasing it.

In some (radially flat and/or sloped) embodiments, the radial or transverse width of the cushion (from inner to outer edge of the cushion) is e.g. about 15-25 millimetres, or more preferably about 17 millimetres to about 23 millimetres, e.g. about 20 millimetres.

In some radially sloped embodiments, the contact surface has generally positive slopes in radial or transverse directions away from the inner opening and/or the centre or centre point of the cushion at or near the first height and/or at or near the second height, and wherein the contact surface has generally negative or declining slopes in radial or transverse directions away from the inner opening and/or the centre or centre point of the cushion at or near the third height and/or at or near the fourth height.

In some radially sloped embodiments, the varying slopes of the contact surface in radial or transverse directions away from the inner opening and/or the centre or centre point of the cushion has a global minimum value near or at a boundary between the lower back-facing part and the lower front-facing part.

Accordingly, the contact surface of the cushion vary radially/transversely providing a radial/transverse slope (in addition to varying about the inner opening and/or the centre or centre point) providing or enabling a fairly complexly shaped contact surface enabling an improved fit to a user's (or an average user's) head shape around an ear of the user in turn providing or enabling increased noise suppression and/or increased user comfort. As disclosed herein, some parts of the contact surface of the cushion may have a positive slope (in outer direction(s)) while other parts of the contact surface of the cushion may have a negative slope (in outer direction(s)). At the third height of the predetermined height profile/a globally lowest valley ('thinnest' part of the cushion) the slope may be negative (in outer direction(s)). At the first and second heights/both peaks, the slope may be positive (in outer direction(s)). This variation enables the cushion to fit a shape of a head of a user to at least a large extent. At the 'thinnest' part of the cushion when properly in place around a user's ear, the size of the chin generally and typically increases with further distance away from the ear whereby—to have an improved fit—the cushion should generally get thinner to fit better or optimally. At the peaks of the contact surface of the cushion, the recesses, indentations, or depressions generally and typically deepens further with further distance away from the ear whereby—to have an improved fit—the cushion should generally get thicker to fit better or optimally. An improved fit will increase noise suppression and/or increase user comfort.

In at least some embodiments, the overall shape of the cushion as seen in the proximal (or in the distal direction) is generally oval. In this way, the shape in this direction is symmetrical, which simplifies manufacturing of the cushion. Alternatively, the overall shape of the cushion as seen in the proximal (or in the distal direction) is irregularly shaped, e.g. more ear-shaped.

In at least some embodiments, the cushion is integrally formed, i.e. formed and manufactured as a single piece. This simplifies manufacturing of the cushion but also further promotes noise suppression (as it is one single cushion without joined parts, etc.) for example compared to cushions being manufactured in separate parts before being joined together. In some embodiments, the cushion may e.g. be manufactured by vacuum forming a sheath, holster, etc. adhering to the shape of the cushion as disclosed herein and filling it with a predetermined material. In at least some embodiments, the predetermined material is a combination of memory foam and a suitable gel.

In some embodiments, the cushion comprises a central (or alternatively radially offset) track, slit, or groove in the contact surface (at least partly but preferably fully) about the centre or centre point. Accordingly, a radially inner part of the cushion is separated from a radially outer part by air whereby ambient sound entering the inside of the cushion has to propagate through air (outside the cushion), the material of the (outer part of the) cushion, air (in the track, slit, or groove), the material of the (inner part of the) cushion, and finally the air (of the inside open space of the cushion) rather than only through air (outside the cushion), the material of the cushion, and finally the air (of the inside open space of the cushion). By having to propagate through additional different mediums and interfaces between them, the sound will be attenuated more increasing the hearing protection capabilities of the cushion.

In some embodiments, the cushion comprises a number of alignment elements arranged on a distal side of the cushion where the alignment elements are further arranged in or according to a predetermined pattern, where the predetermined pattern is asymmetrical in relation to upper and lower directions and/or front-facing and back-facing directions of the cushion. The alignment elements are configured to mate or fit with a number of corresponding alignment elements of an ear cup of a headset and/or hearing protection device that the cushion is to be fitted to. At least some of the alignments of the cushion may protrude from the cushion. In this way, it can be ensured that a particular cushion can only be inserted correctly into an ear cup during assembly or replacement when the respective alignment elements of the cushion and the ear cup align and e.g. mate or connect (since a cushion for a left ear is different than a corresponding cushion for a right ear and to not insert a cushion upside down).

As an overall summary: For embodiments comprising a first, second, third, and a fourth height as disclosed herein and where the contact surface is a generally flat surface in radial or transverse directions away from or towards the inner opening and/or the centre or centre point of the cushion, the first height is a globally largest height/peak (of all height values), the second height is a locally largest height/peak being smaller than the first height, the third height is a globally smallest height/global lowest valley (of all height values), and the fourth height is a locally smallest height/locally lowest valley (with a height value between the second and the third height values).

This will be the case regardless of whether the first, second, third, and/or fourth height values respectively is for inner or outer tracks or parts of the contact surface of the cushion or tracks or parts there-between.

For embodiments comprising a first, second, third, and a fourth height as disclosed herein and where the contact surface is sloped in radial or transverse directions away from or towards the inner opening and/or the centre or centre point of the cushion, the first inner or inner-most height is a globally largest height/peak (of all inner or inner-most height values), the second inner or inner-most height is a locally largest height/peak being smaller than the first inner or inner-most height, the third inner or inner-most height is a globally smallest height/global lowest valley (of all inner or inner-most height values), and the fourth inner or inner-most height is a locally smallest height/locally lowest valley (with an inner or inner-most height value between the second inner or inner-most and the third inner or inner-most height values). This corresponds to the situation for flat embodiments summarised above just with inner values instead of overall values.

and the first outer or outer-most height is a locally largest height/peak (of all outer or outer-most height values), the second outer or outer-most height is a globally largest height/peak being larger than the first outer or outer-most height (and being larger than all height values regardless of whether they are innermost, outermost or for values there-between), the third outer or outer-most height is a globally smallest height/global lowest valley (of all outer or outer-most height values), and the fourth outer or outer-most height is a locally smallest height/locally lowest valley (with an outer or outer-most height value between the second outer or outer-most and the third outer or outer-most height values). For the third and fourth heights, this corresponds to the situation for flat embodiments summarised above just with outer values instead of overall values. For the first and second heights this is different to the situation for flat embodiments summarised above (where the characteristics of the first and second height have been exchanged with respect to being global or local largest heights/peaks).

In some embodiments, the cushion comprises only the global maximum or globally highest peak (the first height) and the global minimum or global lowest valley (the third height) while in alternative embodiments, the cushion comprises the global maximum or globally highest peak (the first height), the local maximum or locally highest peak (the second height) (being smaller than the global maximum or globally highest peak), and the global minimum or global lowest valley (the third height).

In some embodiments, the cushion comprises only the global maximum or globally highest peak (the first height) and the local maximum or locally highest peak (the second height) while in other alternative embodiments, the cushion comprises in addition the global minimum or global lowest valley (the third height) and/or the local minimum or a locally lowest peak (the fourth height).

In some embodiments, the cushion comprises only the global maximum or globally highest peak (the first height) and the local minimum or a locally lowest peak (fourth height) while in other alternative embodiments, the cushion comprises in addition the global minimum or global lowest valley (third height) and/or the local maximum or locally highest peak (the second height).

According to another aspect, a headset and/or a hearing protection device is provided where the headset and/or a hearing protection device comprises at least one ear cup, e.g. two ear cups, wherein at least one ear cup comprises a cushion according to the first aspect.

Further details and embodiments are disclosed in the following.

Definitions

All headings and sub-headings are used herein for convenience only and should not be constructed as limiting the invention in any way.

The use of any and all examples, or exemplary language provided herein, is intended merely to better illuminate the invention and does not pose a limitation on the scope of the invention unless otherwise claimed. No language in the specification should be construed as indicating any non-claimed element as essential to the practice of the invention.

This invention includes all modifications and equivalents of the subject matter recited in the claims appended hereto as permitted by applicable law.

In the present context in relation to the cushion (and the headset and/or hearing protection device comprising such a cushion), the term "distal end" or "distal part" in the appended figures and the present specification is meant to refer to an end or part of the cushion being furthest/further away from a user when wearing a headset and/or hearing protection device comprising the cushion whereas the term "proximal end" or "proximal part" is meant to refer to an opposite end or part being closest/closer to the user when wearing the headset and/or hearing protection device comprising the cushion. "Distal direction" is a direction from the proximal end or part towards the distal end or part, i.e. a direction generally away from the head of the user when wearing the headset and/or hearing protection device, while "proximal direction" is a direction from the distal end or part towards the proximal end or part, i.e. a direction generally towards the head of the user when wearing the headset and/or hearing protection device. Both directions (being parallel and opposite) are illustrated e.g. in FIGS. 1, 2, and 5a. The term "upper part" or "upper direction" of the cushion is meant to refer to the part or direction of the cushion that is closest towards the top of the head of a user when wearing a headset and/or hearing protection device comprising the cushion whereas the term "lower part" or "lower direction" is meant to refer to the part or direction of the cushion that furthest away from the top of the head of a user when wearing a headset and/or hearing protection device comprising the cushion. Both the upper direction and the lower direction are illustrated e.g. in FIGS. 1, 2, 5a, and 9. The upper direction is parallel with and opposite the lower direction. The term "front-facing" is meant to refer to the direction towards the front of the face of a user when wearing a headset and/or hearing protection device comprising the cushion whereas the term "back-facing" is meant to refer to the direction towards the back of the head of a user when wearing a headset and/or hearing protection device comprising the cushion. Front facing is opposite of back-facing. Both the front-facing direction and the back-facing direction are illustrated e.g. in FIGS. 1, 2, 3, 4, 5a, and 9. The term "radial direction" is meant to refer to a planar (i.e. in a predetermined plane substantially perpendicular to the proximal and distal directions) direction radially away from or towards an inner opening (as defined by the cushion) and/or a centre or centre point of the cushion. The term "outer direction" is meant to refer to a radial direction going away from the inner opening and/or the centre or centre point of the cushion, while the term "inner direction" is

DETAILED DESCRIPTION

Various aspects and embodiments of a cushion, as disclosed herein, configured to be secured to an ear cup of a headset and/or hearing protection devices will now be described with reference to the figures.

The shown figures are schematic representations for which reason the configuration of the different structures as well as their relative dimensions are intended to serve illustrative purposes only.

Some of the different components are only disclosed in relation to a single embodiment of the invention, but is meant to be included in the other embodiments without further explanation.

FIGS. 1a-1g respectively schematically illustrates a front (or distal) view, a first (left or back-facing) side view, a second (right or front-facing) side view, a bottom view (in the upper direction), a top view (in the lower direction), a back (or proximal) view, and a perspective view of one exemplary embodiment of a cushion as disclosed herein. Illustrated in FIG. 1 is an embodiment of a cushion 100 as disclosed herein configured to be secured to an ear cup of a headset and/or hearing protection device (see e.g. 301 and 300 in FIG. 10). The shown cushion 100 is for use in connection with a right ear of a user. It is to be understood that a corresponding cushion for use in connection with a left ear of a user is a mirrored version of the shown cushion 100. The cushion 100 comprises a contact surface 101 along a periphery proximal part of the cushion 100 where the contact surface 101 is configured to abut against and contact a user's head around an ear of the user when the headset and/or hearing protection device comprising at least one ear cup with the cushion is worn by the user. The cushion 100 has or defines a central opening 120 and is, in the particular shown embodiment, generally ring shaped as readily seen from the front and back views (FIGS. 1a and 1f) and is, at least in some embodiments, generally oval but may have other suitable shapes. The cushion 100 is integrally formed, i.e. formed and manufactured as a single piece, which further promotes noise suppression.

Figure 1:
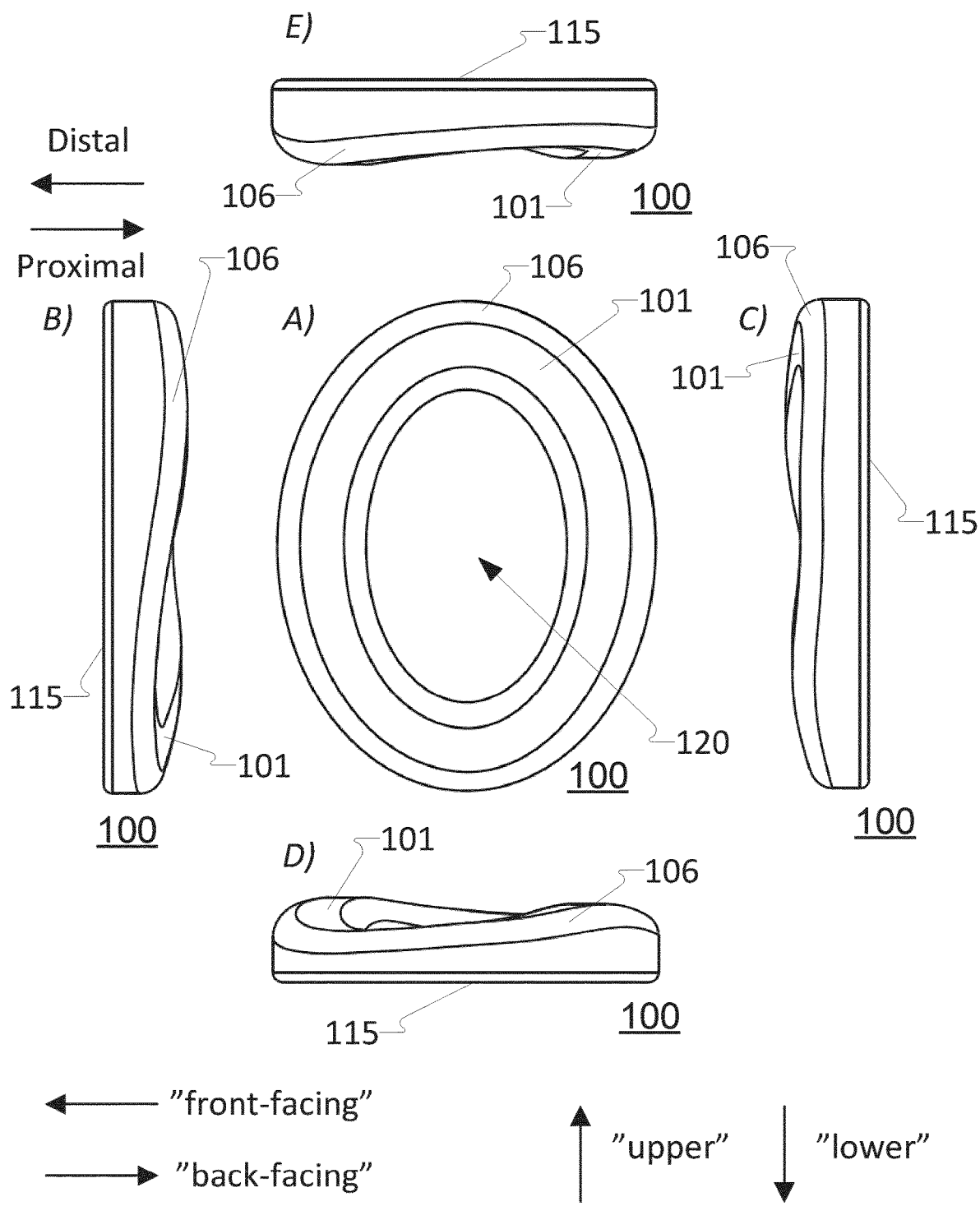
FIGS. 1a-1g respectively schematically illustrates a front, a first (left) side view, a second (right) side view, a bottom view, a top view, a back view, and a perspective view of one exemplary embodiment of a cushion as disclosed herein.
Figure 1:
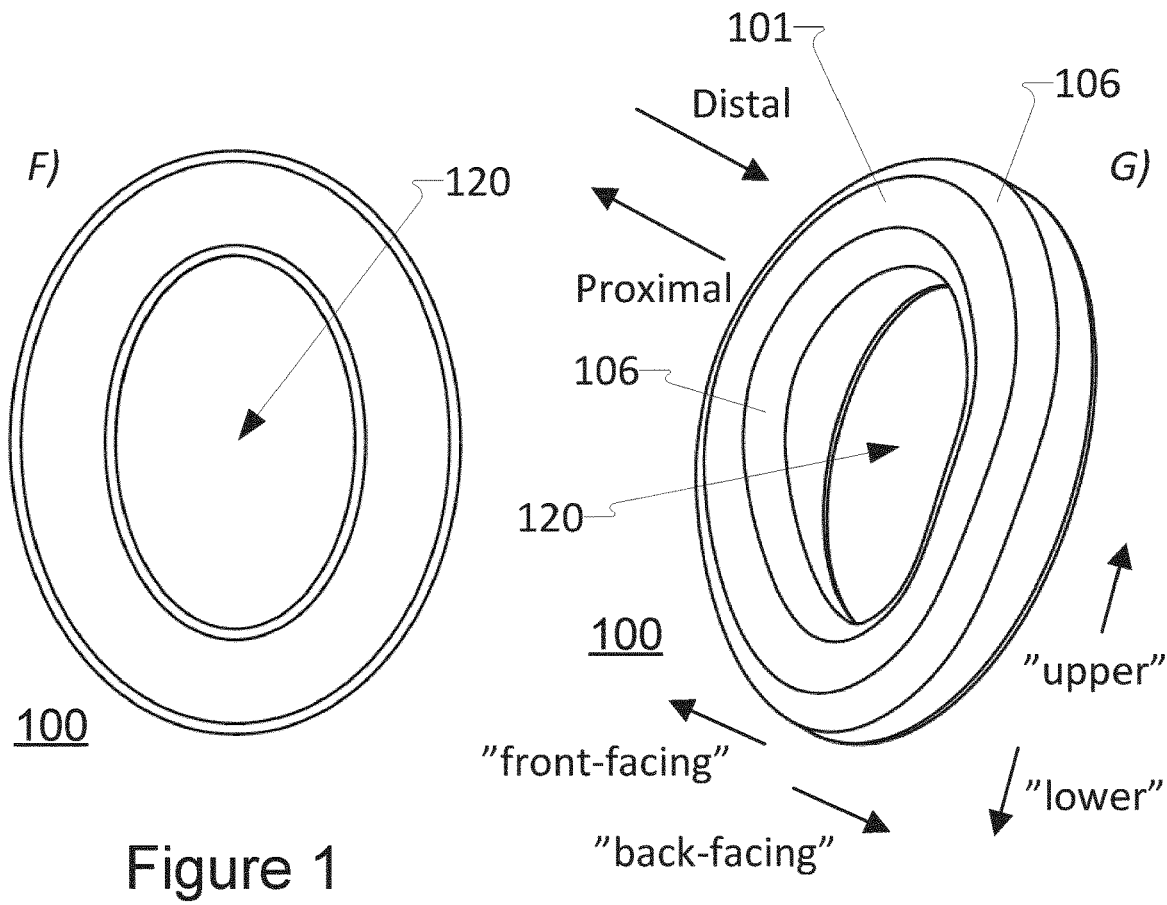

Indicated in FIG. 1 are also (schematic) indications of an upper and lower direction (for FIGS. 1a, 1b, 1c and 1g), a front-facing and a back-facing direction (for FIGS. 1a, 1d, 1e, and 1g), and a distal and a proximal direction (for FIGS. 1b and 1g). While the distal and proximal directions only are illustrated for FIG. 1b (and 1g), corresponding directions are applicable for FIGS. 1c, 1d, and 1e where the respective proximal directions of those Figures are in respective directions (in the layout of FIGS. 1a-e) towards FIG. 1a/the front view and their respective distal directions are in the direction (in the layout of FIGS. 1a-e) away from FIG. 1a/the front view.

As disclosed herein, the shape of the proximal part of the cushion 100 is irregular or non-uniform. More particularly, the contact surface 101 of the cushion 100 has a predetermined height profile (see e.g. 400, 400', 400" in FIGS. 5b and 6a-c) where respective height values of the predetermined height profile at a plurality of locations (see e.g. 110 in FIG. 5a) of the contact surface 101 vary about the inner opening 120 and/or a centre or centre point (see e.g. 130 in FIG. 5a) of the cushion 100.

Figure 3:
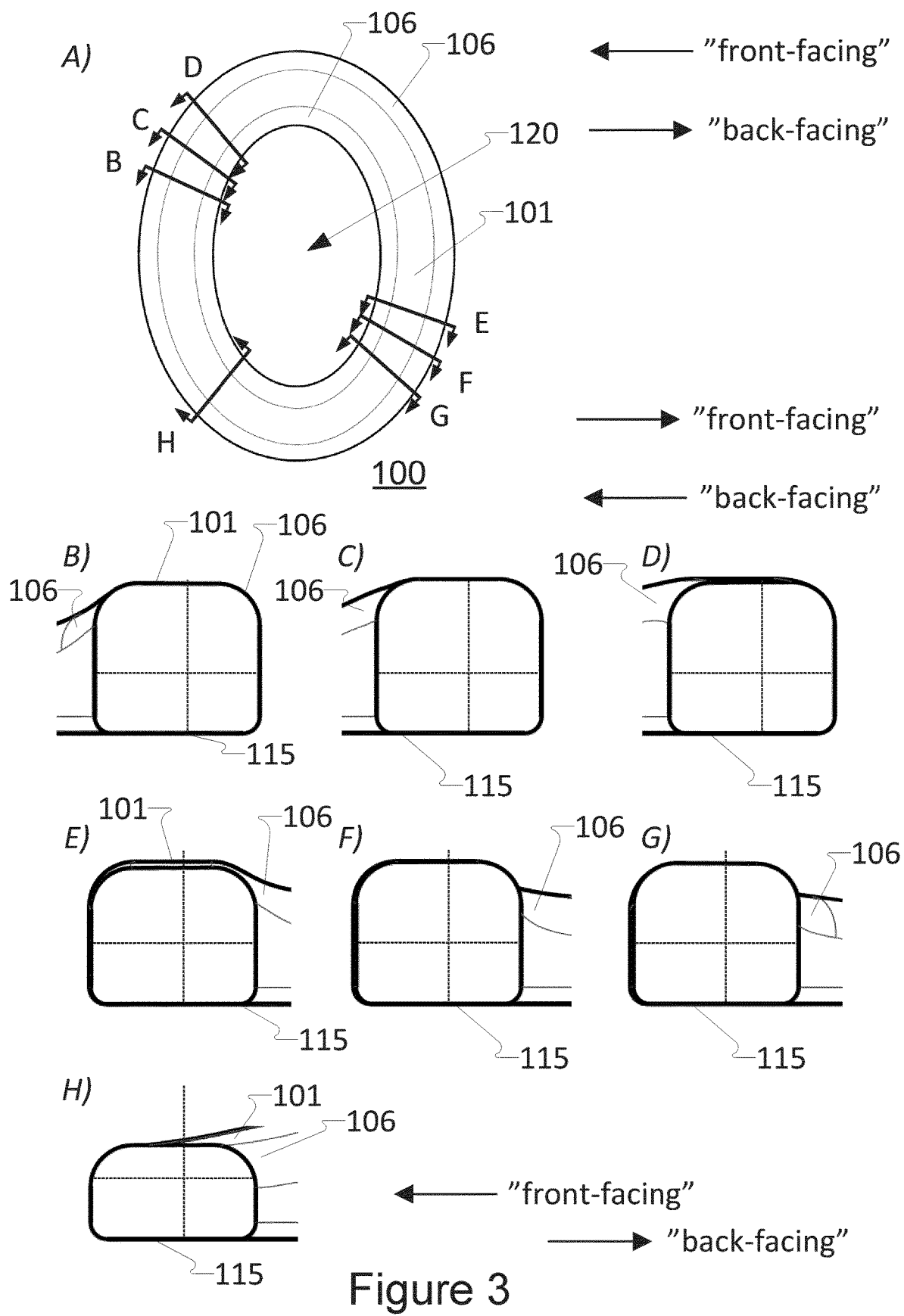
FIG. 3a schematically illustrate a cushion corresponding to the one of FIG. 1 with respective cross-sectional intersections indicated where the cross-sectional views schematically are illustrated in FIGS. 3b-3h.
Figure 4:
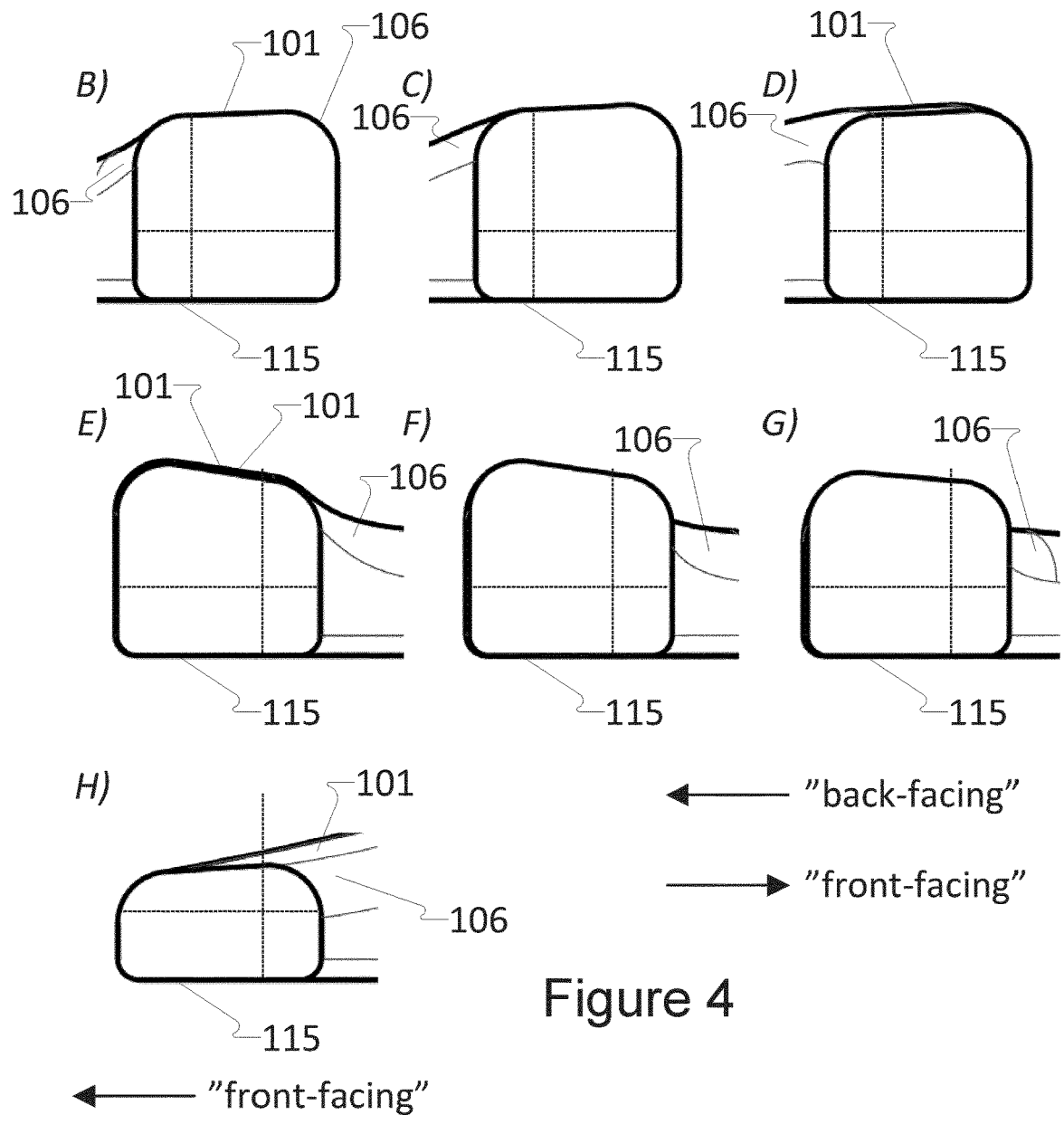
FIGS. 4b-4h schematically illustrate cross-sectional views at corresponding locations as in FIG. 3a of another exemplary embodiment of a cushion as disclosed herein and corresponding to the one illustrated in FIG. 2.

To illustrate the varying heights, FIGS. 3 and 4 illustrates cross-sectional views of a cushion (according to some different embodiments) and FIGS. 5a and 5b, and 6a, 6b, and 6c illustrate the varying heights of the contact surface 101 about the inner opening and/or the centre or centre point at a plurality of different locations along a track on the contact surface 101 at or near the contact surface's proximal circumference.

A first height (see e.g. 410 in FIG. 5b or 410', 410" in FIGS. 6a-c for other alternative embodiments) of the predetermined height profile is a (flat and/or inner) globally largest height of the respective height values at the plurality of locations, i.e. a (flat and/or inner) global maximum or globally highest peak (of the respective heights, where the first height is located in an upper front-facing part (see e.g. segment or quadrant I/102 in FIGS. 5a and 5b or FIGS. 6a-c for other alternative embodiments) of the cushion 100, i.e. located at or near a temple region of a user wearing a headset and/or hearing protection device comprising the cushion 100. This enhances the noise suppression capabilities of the cushion when worn as disclosed herein.

In some further embodiments (and as shown), a second height (see e.g. 420 in FIG. 5b or 420', 420" in FIGS. 6a-c for other alternative embodiments) of the predetermined height profile is a (flat and/or inner) locally largest height of the respective height values, i.e. a (flat and/or inner) local maximum or a locally highest peak (being smaller than the (flat and/or inner) first height/globally highest peak at least in this and corresponding embodiments), where the second height is located in a lower back-facing part (see e.g. segment or quadrant III/104 in FIGS. 5*a* and 5*b* or FIGS. 6*a*-*c* for other alternative embodiments) of the cushion 100, i.e. located at or near a region where the neck is free of the jaw bone of a user wearing a headset and/or hearing protection device comprising the cushion 100.

In some further embodiments (and as shown), a third height (see e.g. 430 in FIG. 5*b* or 430', 430" FIGS. 6*a*-*c* for other alternative embodiments) of the predetermined height profile is a globally smallest height of the respective height values, i.e. a global minimum or a global lowest valley, where the third height is located in a lower part (see e.g. segments or quadrants II/103 and III/104 in FIGS. 5*a* and 5*b* or FIGS. 6*a*-*c* for other alternative embodiments) of the cushion 100, i.e. located at or near a region underneath the ear of a user wearing a headset and/or hearing protection device comprising the cushion 100. In some further embodiments, the third height is more specifically located in a lower front-facing part (see e.g. segment or quadrant II/103 in FIGS. 5*a* and 5*b* or FIGS. 6*a*-*c* for other alternative embodiments) of the cushion 100, i.e. located at or near a region where the upper part of the jaw bone of a user, wearing a headset and/or hearing protection device comprising the cushion 100, is located.

In some embodiments, the cushion 100 comprises only the global maximum or globally highest peak (see e.g. 410, 410', 410") and the global minimum or global lowest valley (430, 430', 430") while in alternative embodiments, the cushion 100 comprises the global maximum or globally highest peak (see e.g. 410, 410', 410"), the local maximum or locally highest peak (see e.g. 420, 420', 420") (being smaller than the global maximum or globally highest peak), and the global minimum or global lowest valley (see e.g. 430, 430', 430").

In some embodiments, the cushion 100 comprises only the global maximum or globally highest peak (see e.g. 410, 410', 410") and the local maximum or locally highest peak (see e.g. 420, 420', 420") while in other alternative embodiments, the cushion 100 comprises in addition the global minimum or global lowest valley (see e.g. 430, 430', 430") and/or the local minimum or a locally lowest peak (see e.g. 440, 440', 440").

In some further embodiments (and as shown), a fourth height (see e.g. 440 in FIG. 5*b* or 440', 440" in FIGS. 6*a*-*c* for other alternative embodiments) of the predetermined height profile is a locally smallest height of the respective heights, i.e. a local minimum or a locally lowest valley, where the fourth height is located in a back-facing part (see e.g. segments or quadrants III/104 and IV/105 in FIGS. 5*a* and 5*b* or FIGS. 6*a*-*c* for other alternative embodiments) of the cushion 100. In some further embodiments, the fourth height is located in an upper back-facing part (see e.g. segment or quadrant IV/105 in FIGS. 5*a* and 5*b* or FIGS. 6*a*-*c* for other alternative embodiments) of the cushion 100.

In some embodiments, the cushion 100 comprises only the global maximum or globally highest peak (see e.g. 410, 410', 410") and the local minimum or a locally lowest peak (see e.g. 440, 440', 440") while in other alternative embodiments, the cushion 100 comprises in addition the global minimum or global lowest valley (see e.g. 430, 430', 430") and/or the local maximum or locally highest peak (see e.g. 420, 420', 420").

According to some embodiments (and as shown), the contact surface 101 has a generally flat surface (see e.g. FIGS. 3*a*-*h*) in one or more radial/transversal directions (i.e. one or more directions (substantially perpendicular to the proximal and distal directions) from or away the inner opening 120 and/or a centre or centre point of the cushion), e.g. with a small rounding 106 at or near the edges of the contact surface. In other words, the contact surface 101 is generally radially/transversely flat but still varies about the inner opening 120 and/or the centre or centre point of the cushion. Alternatively, the contact surface 101 has slopes (see e.g. FIGS. 4*b*-*h*), at least at some locations, in radial or transverse directions away from or towards the inner opening 120 and/or centre or centre point (see e.g. 130 in FIG. 5*a*) of the cushion 100 (see e.g. FIGS. 2, 3*a* together with 4*b*-*h*), i.e. the contact surface 101 is slanted or tapers away towards the inner opening 120 and/or the centre or centre point at some locations and is slanted or tapers away in the opposite radial/transversal direction at other locations (see e.g. FIG. 7).

The drawn lines indicating or delimiting the contact surface 101 from the rounding 106 and the rest of the cushion 100 are not meant to (necessarily) indicate a sharp edge (but can) but rather to indicate a curvature of the cushion. The same applies for the two inner drawn lines of the back views (see e.g. FIG. 1*f*) and the drawn lines between the contact surface 101 and the bottom or lower surface 115. This applies for all relevant drawings.

FIGS. 2*a*-2*g* respectively schematically illustrates a front, a first (left) side view, a second (right) side view, a bottom view, a top view, a back view, and a perspective view of another exemplary embodiment of a cushion as disclosed herein.

The cushion 100 of FIGS. 2*a*-2*g* correspond to the one except than instead of having the contact surface 101 having a generally radial/transverse flat surface, the contact surface 101, in this and corresponding embodiments, is radially/transversally sloped (in addition to varying about the inner opening 120 and/or the centre or centre point of the cushion) as disclosed herein and e.g. as seen in FIG. 4*b*-*h*. Exemplary varying height profiles for the contact surface of such an embodiment having a radially sloped contact surface 101 is e.g. illustrated in FIGS. 6*a*-*c* where FIG. 7 illustrates varying radial slopes.

An advantage of a radially sloped contact surface 101 over a flat is that it may offer even further increased user comfort (by avoiding or at least decreasing local 'pressure points') and/or may also more closely follow the shape of a user's head when worn (where wearing causes the cushion to tilt) thereby increasing noise suppression further of the cushion 100. A cushion with a contact surface having a generally radially flat surface may on the other hand be simpler to produce.

FIG. 3*a* schematically illustrate a cushion corresponding to the one of FIG. 1 (and FIG. 2) with respective cross-sectional intersections indicated where the cross-sectional views schematically are illustrated in FIGS. 3*b*-3*h*. Illustrated in FIG. 3*a* is a cushion 100 corresponding to the one of FIG. 1 where the contact surface 101 has a generally flat contact surface 101 with rounded radial/transverse edges 106 and where a number of cross-sectional intersections respectively labelled B, C, D, E, F, G, H are indicated where the corresponding cross-sectional views respectively are show in FIG. 3*b* (intersection labelled B), 3*c* (intersection C), 3*d* (intersection D), etc.

Intersections B, C, D are located at and around the first height/globally highest peak (see e.g. 410 in FIG. 5*b*), i.e. in the upper front-facing part (see e.g. segment or quadrant I:/102 in FIGS. 5*a* and 5*b*) of the cushion 100, while intersections E, F, G are located at and around the second height/locally highest peak (see e.g. 420 in FIG. 5*b*), i.e. in the lower back-facing part (see e.g. segment or quadrant III:/104 in FIGS. 5*a* and 5*b*) of the cushion 100, and finally intersection H is located at or near the third height/global lowest valley (see e.g. 430 in FIG. 5*b*), i.e. in the lower front-facing part (see e.g. segment or quadrant II:/103 in FIGS. 5*a* and 5*b*) of the cushion 100.

FIGS. 3*b-d* illustrate details of the first height/globally highest peak (see e.g. 410 in FIG. 5*b*) in the upper front-facing part of the cushion 100 where FIG. 3*c* illustrates the largest height (of the three), while FIGS. 3*e-g* illustrate details of the second height/locally highest peak (see e.g. 420 in FIG. 5*b*) in the lower back-facing part of the cushion 100. In the shown embodiment and from the cross-sectional views it can be seen that the second height/locally highest peak is smaller than the first height/globally highest peak and that the peak around the second height has a smaller extent than the peak around the first height.

FIG. 3*h* illustrate details of the third height/global minimum or a global lowest valley in the lower front-facing part of the cushion 100.

Indicated (by the two dotted/dashed crossing lines) in each of FIGS. 3*b-d* is the largest height and width (being those of FIG. 3*c* in the shown examples). As can be seen, the height is larger for FIG. 3*c* (as the vertical dotted/dashed line extends above the heights of the contact surface 101 for the other figures). As can be further seen the (radial) width is the same for all cross-sections. In other embodiments, the (radial) width may vary.

Figure 5B:
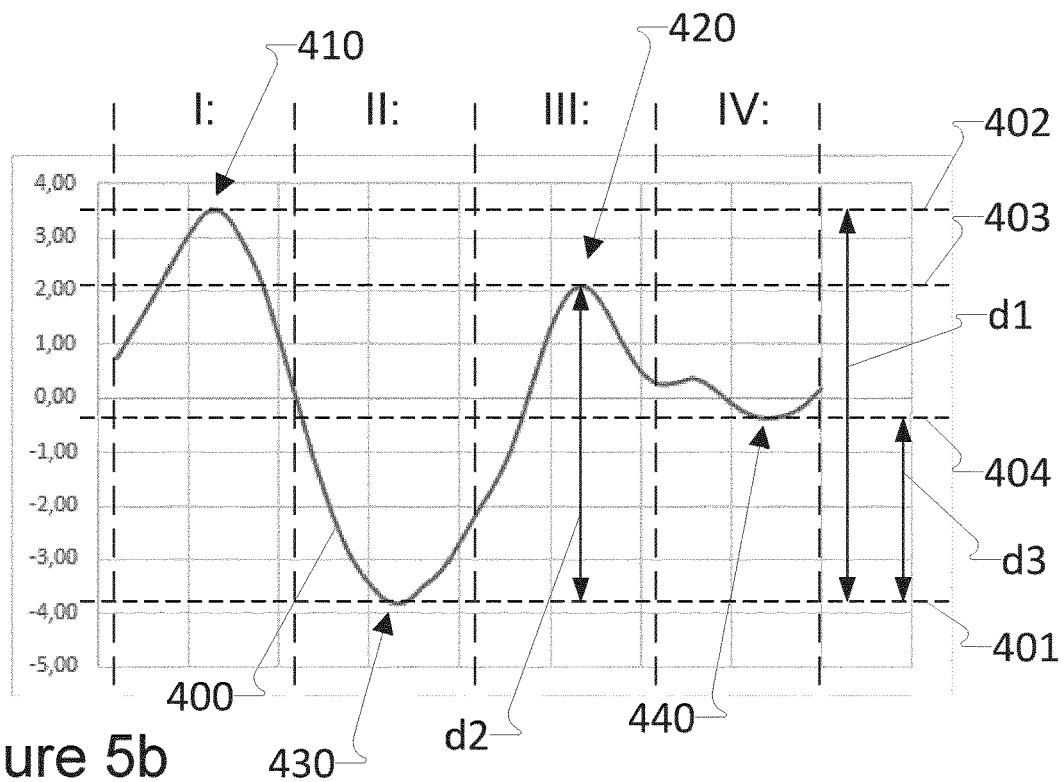
FIG. 5b schematically illustrates a varying height profile of a cushion according to one embodiment as obtained by registering height values at measurements points (where some are indicated in FIG. 5a)
Figure 5A:
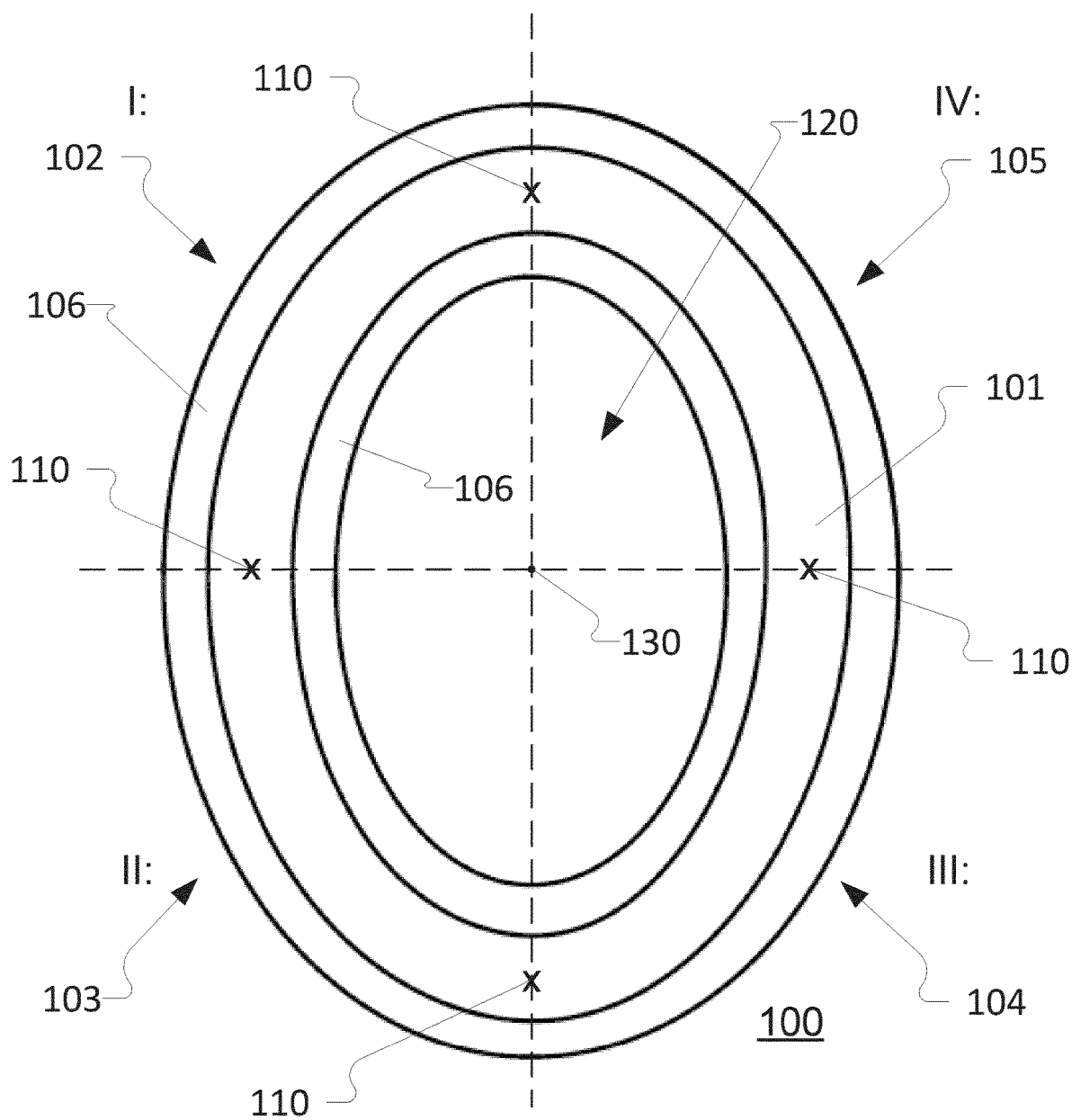
FIG. 5a schematically illustrates a front view corresponding to that of FIG. 1 where (some) measurement points have been indicated for explanatory purposes.
Figure 5A:
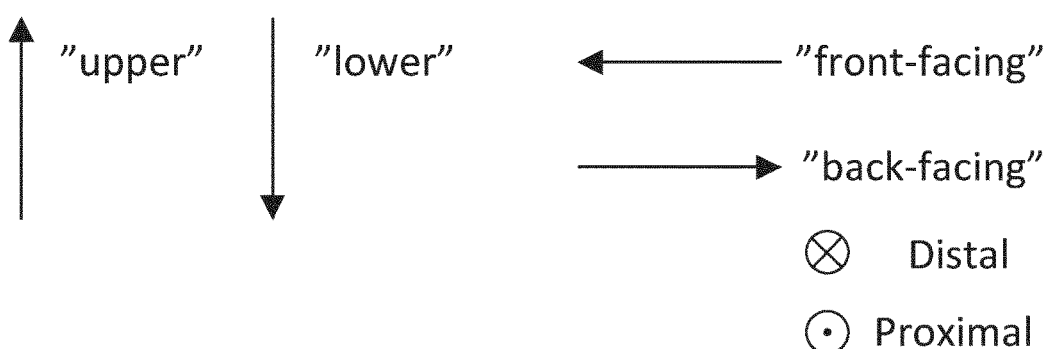

Further details and characteristics of the varying heights and respective peaks and valleys are given herein and e.g. in connection with FIGS. 5*a* and 5*b*

FIGS. 4*b*-4*h* schematically illustrate cross-sectional views at corresponding locations as in FIG. 3*a* of another exemplary embodiment of a cushion as disclosed herein. The cushion that the cross-sectional views are for correspond to the one of FIG. 2 where the contact surface 101 has a generally radial/transversal sloped surface in at least one radial direction away from or towards an inner opening and/or a centre or centre point of the cushion rather than a generally flat radial/transversal surface. The cross-sectional intersections for the cross-sectional views of FIGS. 4*b*-4*h* are at the same locations as indicated in FIG. 3*a* where the corresponding cross-sectional views respectively are show in FIG. 4*b* (intersection labelled B), 4*c* (intersection C), 4*d* (intersection D), etc.

Like for FIG. 3, details of the first (inner) height/globally highest peak (see e.g. 410' in FIG. 6*a*) in the upper front-facing part (see e.g. segment or quadrant I:/102 in FIGS. 6*a-c* and FIG. 5*a*) of the cushion, the (smaller) second (inner) height/locally highest peak (see e.g. 420' in FIG. 6*a*) in the lower back-facing part (see e.g. segment or quadrant III:/104 in FIGS. 6*a-c* and FIG. 5*a*) of the cushion 100, and the third (inner) height/global lowest valley (see e.g. 430' in FIG. 6*a*) in the lower front-facing part (see e.g. segment or quadrant II:/103 in FIGS. 6*a-c* and FIG. 5*a*) of the cushion 100 are shown in FIG. 4. In the shown embodiment, the cushion comprises rounded radial/transverse edges 106.

Figure 2:
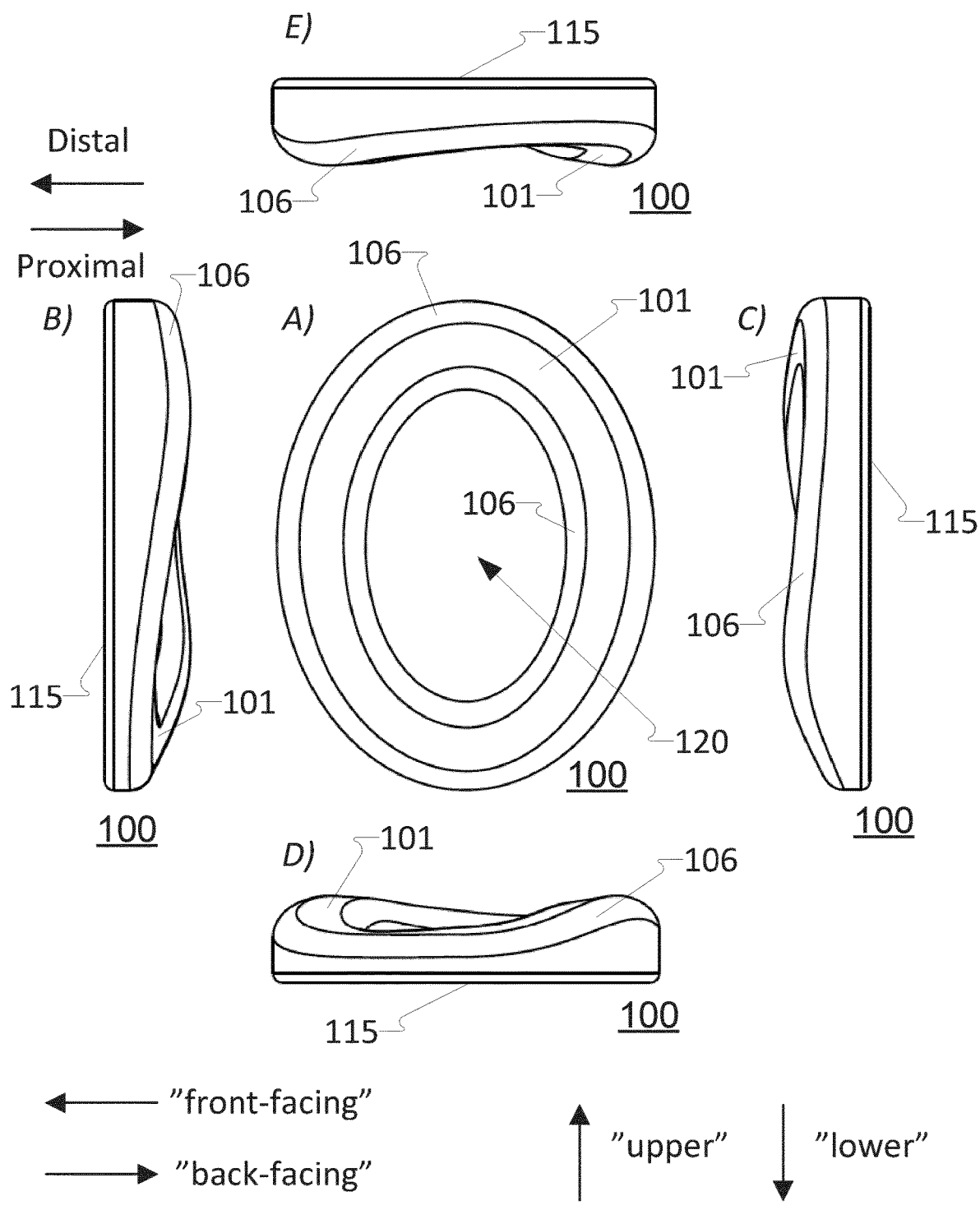
FIGS. 2a-2g respectively schematically illustrates a front, a first (left) side view, a second (right) side view, a bottom view, a top view, a back view, and a perspective view of another exemplary embodiment of a cushion as disclosed herein.
Figure 2:
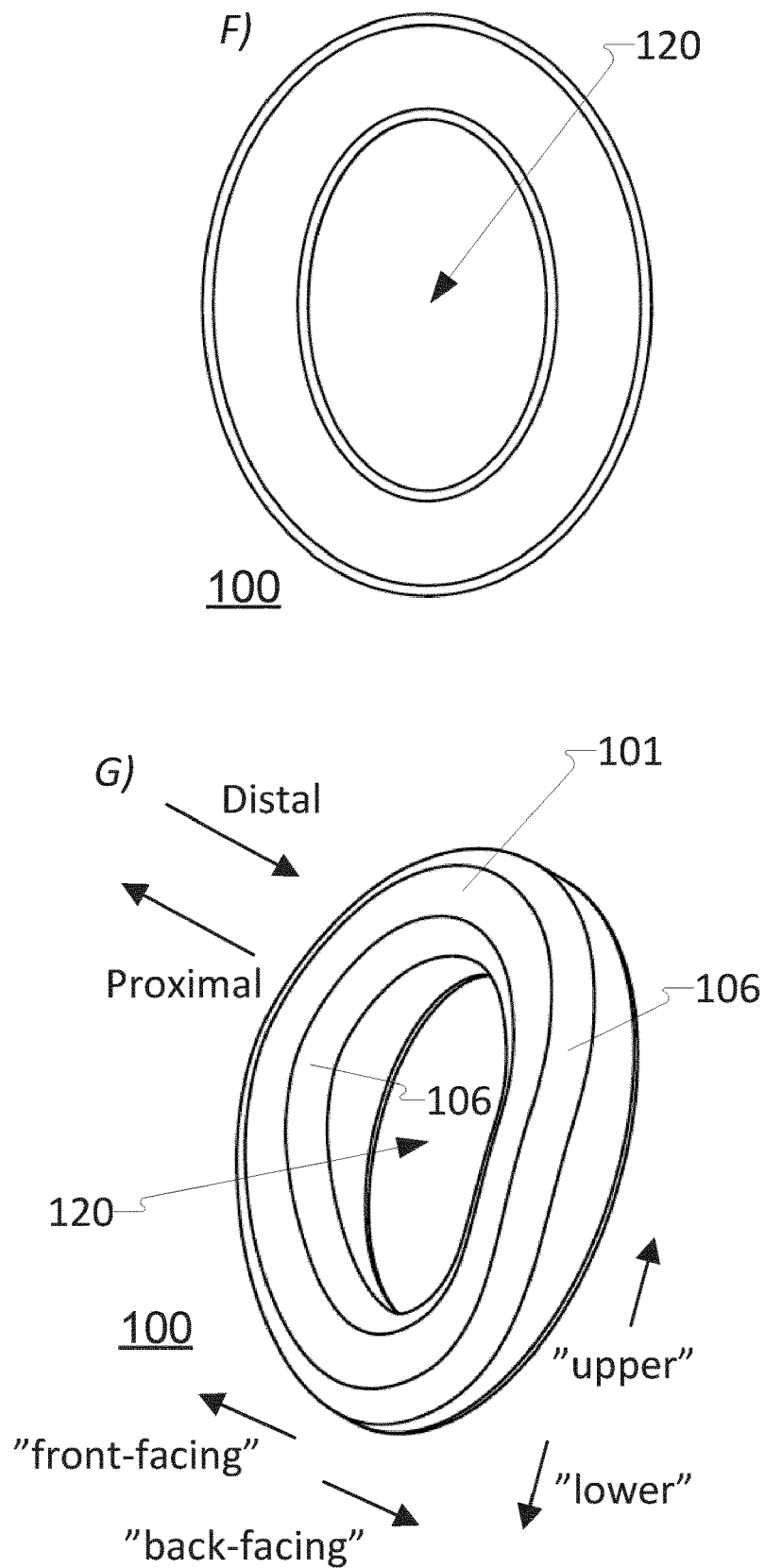

It is noted that the actual values of the respective first, second, third, and fourth heights will vary radially depending on where (in a radial or transversal direction from or away the centre or centre point) the contact surface 101 they respectively are provided for, i.e. it depends whether a value is provided for a middle track or part, an outer (further or furthest away from the centre or centre point) track or part, an inner (closer or closest towards the centre or centre point) track or part, etc. of the contact surface 101 due to the sloped nature or otherwise radially non-flat surface of the contact surface 101 for embodiments such as shown in FIGS. 2 and 4. This is shown and explained in more detail in connection with FIGS. 6*a-c*. As mentioned, this does not apply for embodiments where the contact surface 101 is generally radially/transversely flat (as e.g. is the case for FIGS. 1 and 3).

The radially sloped contact surface 101 may have a general negative or declining slope, at least at some (in the shown example most) or all locations, in a radial direction away from an inner opening and/or a centre or centre point of the cushion. This is the case for the cross-sections of FIGS. 4*b-g*. At other locations, the sloped contact surface 101 may have a general positive inclining slope in a radial direction away from a centre or centre point of the cushion (being the same as having a general negative or declining slope in a radial direction towards the centre or centre point of the cushion). This is the case for the cross-section of FIG. 4*h*. Accordingly, at some locations (at most locations, at least according to some embodiments and as shown) the outer height is greater than the inner height (as is the case for FIGS. 4*b-g*) and at other locations (at less locations, at least according to some embodiments and as shown) the outer height is smaller than the inner height (as is the case for FIG. 4*h*).

FIG. 5*a* schematically illustrates a front view corresponding to that of FIG. 1*a* (or alternatively 2*a*) where (some) measurement points have been indicated for explanatory purposes.

Illustrated is a front or distal view of a cushion 100 as disclosed herein (for a right ear of a user) where an upper front-facing part 102 (also referred to as segment or quadrant I:), a lower front-facing part 103 (also referred to as segment or quadrant II:), a lower back-facing part 104 (also referred to as segment or quadrant III:), and an upper back-facing part 105 (also referred to as segment or quadrant IV:) of the cushion 100 are illustrated. The parts/quadrants 102, 103, 104, 105/I:, II:, III:, IV: divide the cushion 100 in equally large parts. Broken straight lines going through a centre or centre point 130 of the cushion illustrate the division between the parts or segments/quadrants. Also indicated are the upper, lower, front-facing, back-facing, distal, and proximal directions. The illustrated embodiment of FIG. 5*a* is a radially or transversally flat embodiment.

Further indicated are a number (here four) exemplary locations or measurement points 110 distributed on the contact surface 101 about the shown inner opening 120 and the centre or centre point 130 (coinciding in the shown embodiment with the centre of the inner opening 120) of the cushion 100 that may be used to obtain a graph or profile of respective heights as shown in FIG. 5*b* (or 6*a-c*). In the particular shown embodiment, the cushion 100 is rounded by roundings 106 at or near the inner and outer edges of the contact surface 101. Alternatively, the cushion is not rounded, whereby the transition from the contact surface 101 towards the back of the cushion will be with sharper angles. The exemplary locations or measurement points 110 are, in the particular shown embodiment located, centrally (in radial directions) on the contact surface 101, but since the contact surface 101 is radially flat it does not matter where the locations or measurement points 110 radially are located on the contact surface 101. To obtain the graph or profile of FIG. 5*b* more locations or measurement points 110 have been used but only some are indicated in this figure. The graph or profile of FIG. 5*b* gives a detailed view of how the contact surface 101 (the respective heights thereof) varies when traversing the contact surface 100 about the inner opening 120 and/or the centre or centre point 130 for a radially flat embodiment.

FIG. 5b schematically illustrates a varying height profile of a cushion according to one embodiment as obtained by registering height values at measurements points (where some are indicated in FIG. 5a). Illustrated is a graph or height profile of respective heights 400 of a contact surface of a cushion as disclosed herein where the respective heights 400 at various locations (see e.g. 110 in FIG. 5a) of the contact surface about an inner opening (as defined by the cushion) (see e.g. 120 in FIG. 5a) and/or a centre or centre point (see e.g. 130 in FIG. 5a) of the cushion have been plotted. The graph or height profile of respective heights 400 is for a cushion with a contact surface having a generally radially flat surface in directions away from or towards the centre or centre point of the cushion and more specifically for a cushion corresponding to the ones illustrated in FIGS. 1 and 3. One exception is that the graph or height profile of respective heights 400 has been obtained for a non-rounded cushion, which influences the height values as mentioned herein. The location for the beginning of the profile starts in this particular example with the upper central location (see uppermost location or measurement point 110 in FIG. 5a) and traverses, as an example, anti-clockwise about the inner opening and/or centre or centre point of the cushion. For radially flat contact surfaces it does not matter whether the heights are measured at a central track (as is the case of the present example), near the outer edge, or near the inner edge of the contact surface as long as it is not at the edges if the edges are rounded. If the edges are rounded, it does not matter (for radially flat embodiments) where the heights are measured as long as it is on the contact surface (between the rounded edges). As mentioned, this is different for embodiments with a radially sloped contact surface as the height varies radially (in a radial direction to/from the inner opening and/or centre or centre point of the cushion). However, even for sloped contact surface as disclosed herein, it is not as significant (in the radial direction) where (inner, central, outer, etc.) the contact surface measurements are made as long as it done consistently (inner, central, outer, etc.). What is at least more significant is the locations of peaks and valleys, the height relationship between them, and how the contact surface (i.e. its height) varies about the inner opening and/or the centre or centre point of the cushion.

The x-axis of the graph or profile simply shows the locations or points traversing the contact surface about the inner opening and/or centre or centre point while the y-axis illustrates respective height values at the locations or points associated with the x-axis where the y-axis scale is in relation to a neutral level of a head of a user (or a neutral level as averaged for a plurality of users), i.e. a positive value on the y-axis signifies a recess on the head of a user while a negative on the y-axis value signifies a protrusion on the head of the user that the contact surface variation of the cushion is to accommodate to (and/or influence in order to increase noise suppression of the cushion) even taking into account that the cushion will be tilted during use.

The graph or profile of respective heights 400 clearly indicates how the contact surface varies about the inner opening and/or centre or centre point. Further indicated with labels I:, II:, III:, and IV: are which respective heights of the predetermined height profile 400 belong to what part, segment, or quadrant (see e.g. 102, 103, 104, and 105 in FIG. 5a). The graph or predetermined height profile 400 clearly indicates a first height 410 being a globally largest height of the respective heights, i.e. a global maximum or globally highest peak, to be in part I:, a (smaller) second height 420 being a local maximum or a locally highest peak to be part in III:, a third height 430 being a globally smallest height of the respective heights, i.e. a global minimum or a global lowest valley to be in part II:, and a fourth height 440 being a locally smallest height of the respective heights, i.e. a local minimum or a locally lowest valley, to be in part IV:.

Further indicated are a level of the third height 401, a level of the first height 402, a level of the second height 403, a level of the fourth height 404, and respective differences in height d1, d2, and d3. The respective differences in heights d1 (first difference 402), d2 (second difference 403), and d3 (the fourth difference 404) are indicated or given in relation to the height level or value of the third height 401 (i.e. the lowest height) as what is relevant in this respect is their individual relative differences in height (together with the height variation about the inner opening and/or centre or centre point); not their overall absolute size in relation to a total thickness of the cushion.

In some embodiments where the contact surface is generally flat in radial directions away from or towards the centre or centre point, d1 is about 5 mm (millimetres) to about 10 mm, or more preferably about 6 mm to about 8 mm, e.g. about 7 mm.

In some embodiments where the contact surface is generally flat in radial directions away from or towards the centre or centre point, d2 is about 3 mm to about 9 mm, or more preferably about 5 mm to about 7 mm, e.g. about 6 mm (all under the condition that d2 is less than d1).

In some embodiments where the contact surface is generally flat in radial directions away from or towards the centre or centre point, d3 is about 1 mm to about 6 mm, or more preferably about 2 mm to about 4 mm, e.g. about 3 mm (all under the condition that d3 is less than d2).

As can be seen, the contact surface variation or the profile of the cushion in the upper back-facing part IV: comprises, at least in the shown and corresponding embodiments, a non-monotonic segment.

Figure 6A:
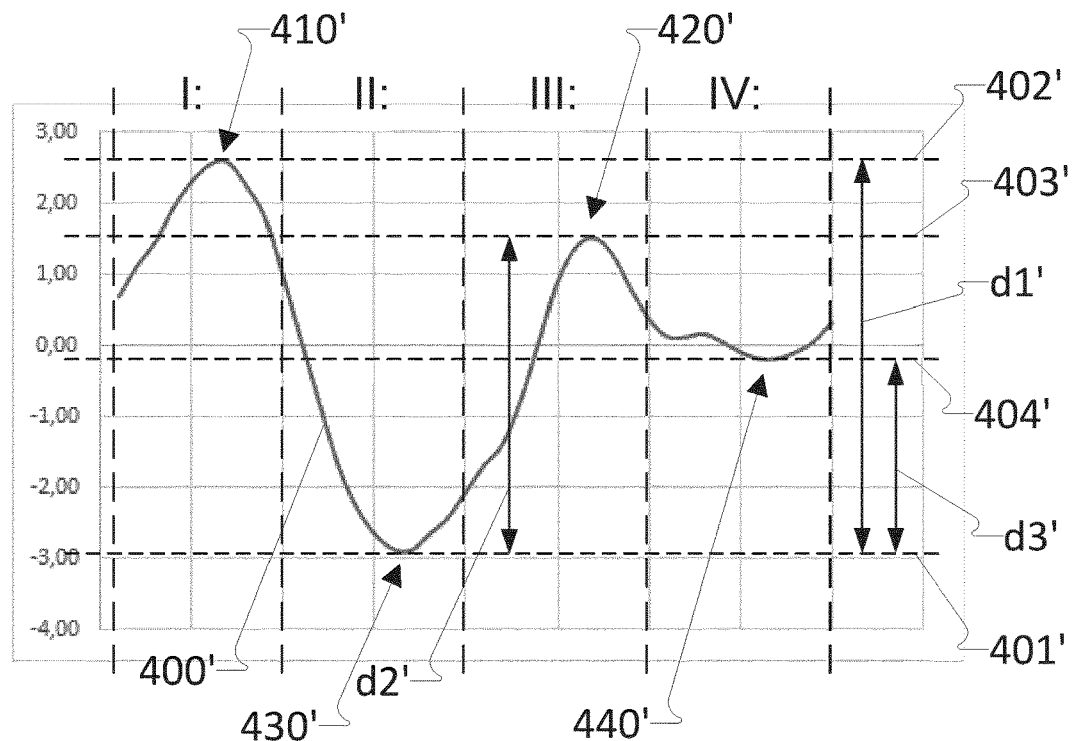
FIGS. 6a and b schematically illustrate varying height profiles of a cushion according to another embodiment as obtained by registering height values at measurements points.
Figure 7:
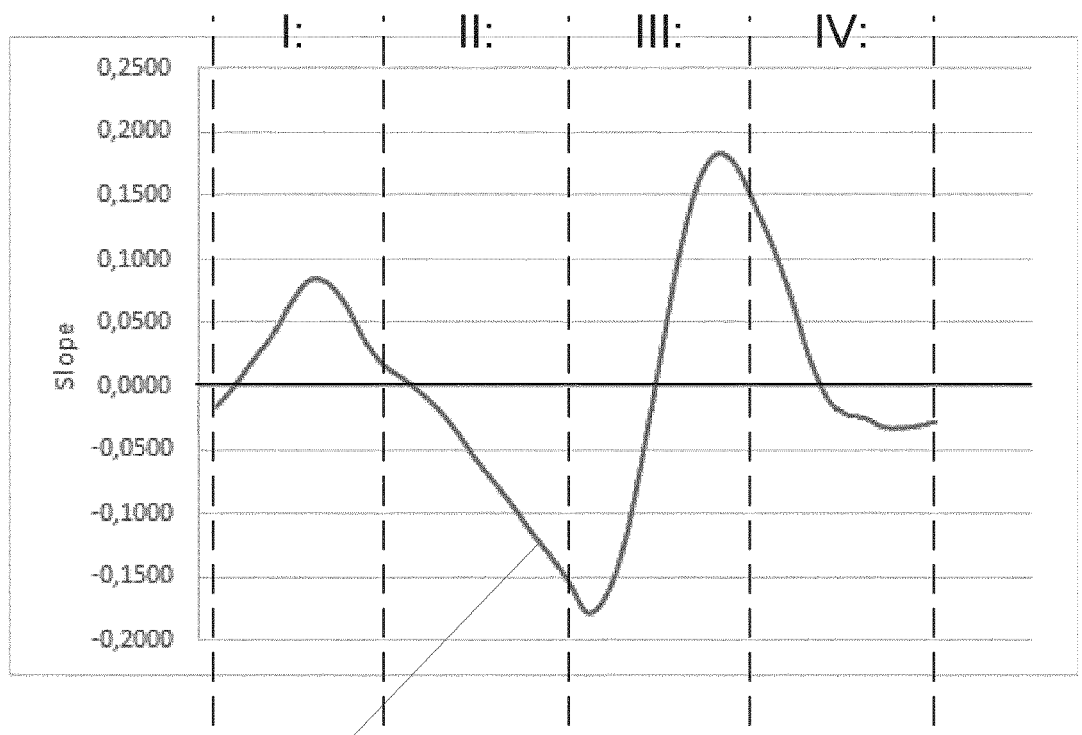
FIG. 7 schematically illustrates varying radial slopes of a cushion according to one embodiment as obtained by registering slope values at measurements points.
Figure 9:
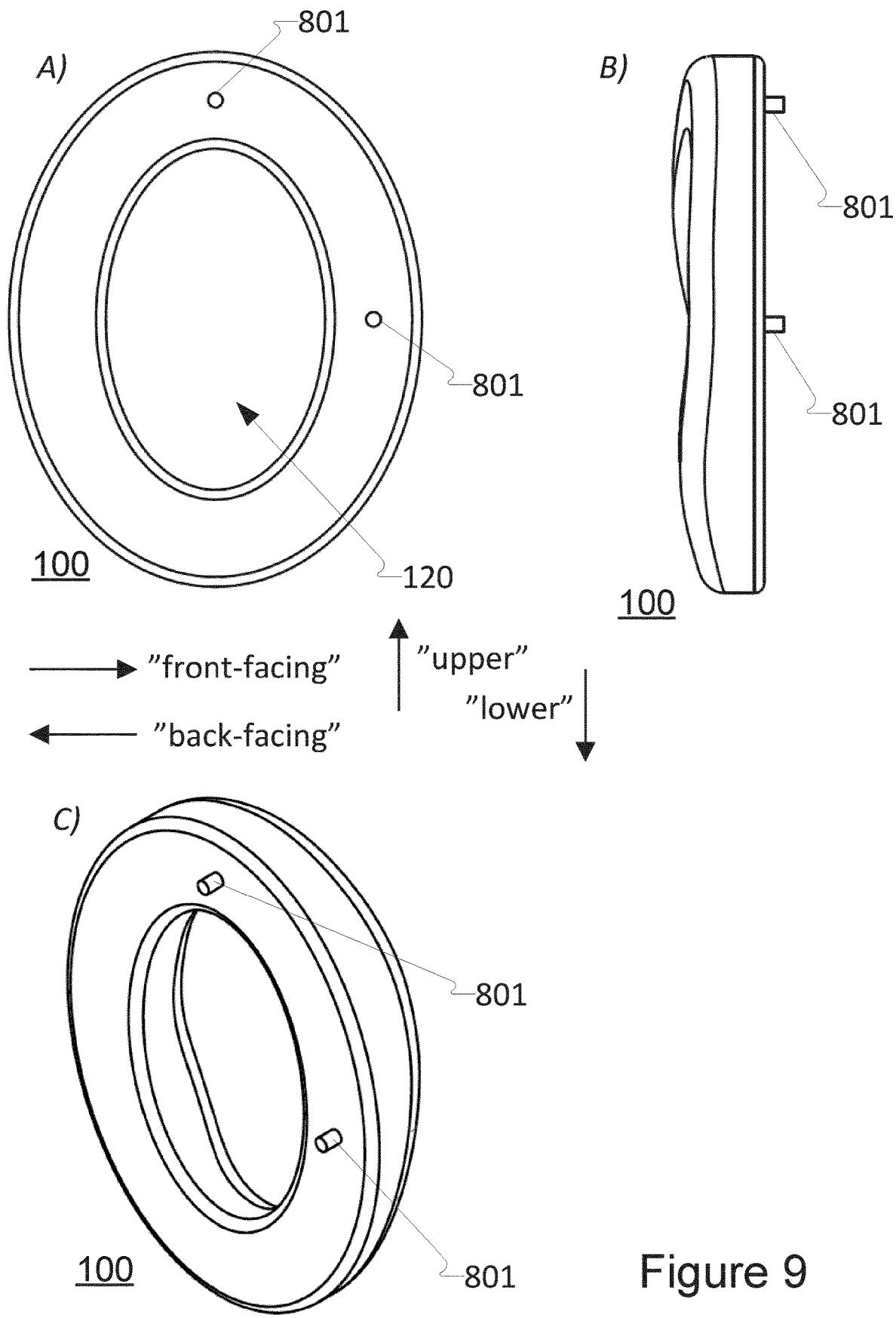
FIGS. 9a-c schematically illustrates different views of a cushion according to alternative embodiments.

FIGS. 6a and b schematically illustrate varying height profiles of a cushion according to another embodiment as obtained by registering height values at measurements points.

The varying height profiles of FIGS. 6a and 6b correspond to the varying height profile of FIG. 5b except as noted in the following (since these figures are for a cushion having a radially sloped contact surface rather than a radially flat contact surface as in FIG. 5b).

Due to a radially sloping contact surface (at least at some locations)—where the height will be different depending on where the locations or measurement points 110 are distributed radially or transversally on the contact surface 101—one graph or predetermined height profile of respective heights 400' (shown in FIG. 6a) of a contact surface of a radially sloped cushion as disclosed herein is illustrated for respective heights 400' at various locations about an inner opening and/or a centre or centre point all being located at an inner (i.e. closest or closer towards the centre or centre point) track or part of the contact surface 101 and another graph or predetermined height profile of respective heights 400" (shown in FIG. 6b) is illustrated for the same cushion at an outer (i.e. furthest or further on the contact surface away from the inner opening and/or centre or centre point) track or part. Height values for radial locations between these (inner and outer), e.g. for a middle or central track or part, will be somewhere between (depending on the value of the slope) the values of the inner and outer parts or tracks. Difference in respective heights between a point in 6a and 6b gives the radial slope at that point (see e.g. also FIG. 7). More specifically, the graphs or height profiles of FIGS. 6a and *b* are for a radially sloped cushion corresponding to the one shown in FIGS. 2 and 4, but where the cushion the graphs or height profiles of FIGS. 6a and *b* are for a non-rounded cushion.

Shown in FIG. 6a is a graph or predetermined height profile 400' of inner heights 400' obtained by traversing a cushion about an inner opening and/or centre or centre point at an inner track or part of a contact surface. As can be seen, the graph or height profile 400' indicates a first inner height 410' being an inner globally largest height of the respective heights, i.e. an inner global maximum or inner globally highest peak, to be in part I:, a (smaller) second inner height 420' being an inner local maximum or an inner locally highest peak to be part in III:, a third inner height 430" being an inner globally smallest height of the respective heights, i.e. an inner global minimum or an inner global lowest valley to be in part II:, and a fourth inner height 440' being an inner locally smallest height of the respective heights, i.e. an inner local minimum or an inner locally lowest peak, to be in part IV:.

Additionally, a first, second, and third inner difference in height (d1', d2', and d3') are each indicated in relation to the level 401' of the third inner height 430'/the global minimum or the global lowest valley in part II:, where d1' is larger than each of d2' and d3' and d2' each is larger than d3'. The graph or height profile 400' corresponds in overall shape to the graph or height profile 400 of FIG. 5b.

Figure 6B:
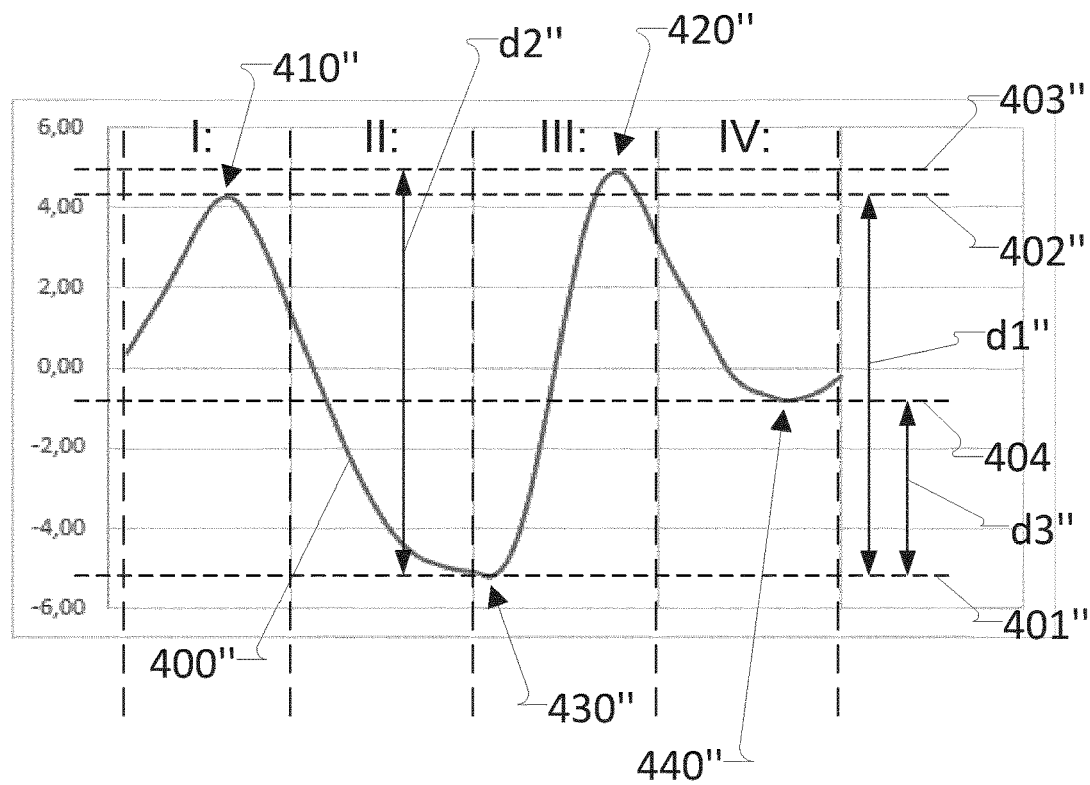
FIG. 6c schematically illustrates both the varying height profiles of FIGS. 6a and 6b shown together.

Shown in FIG. 6b is a graph or profile 400" obtained by traversing a cushion about the inner opening and/or the centre or centre point at an outer track or part of outer heights 400". As can be seen, the graph or predetermined height profile 400" of outer heights 400" indicates a first outer height 410" being an outer locally largest height of the respective heights, i.e. an outer local maximum or outer locally highest peak, to be in part I:, a (larger) second outer height 420' being an outer global maximum or an outer globally highest peak to be part in III:, a third outer height 430" being an outer globally smallest height of the respective heights, i.e. an outer global minimum or an outer global lowest valley to be in part III:, and a fourth outer height 440' being an outer locally smallest height of the respective heights, i.e. an outer local minimum or an outer locally lowest peak, to be in part IV:.

As can further be seen (see also FIG. 6c), the inner height values of graph or height profile 400' are generally different (generally lower at the peaks and higher at the valleys) than the corresponding outer values of graph or height profile 400". Additionally, it can be seen that in 400" it is the second outer height 420" that is the globally largest height value (rather than the first inner height 420' in 400', which then is a locally largest height value). In other embodiments, this may be different, e.g. the second outer height 420" may be smaller than the first outer height 410" or they may also be (about) equal size. The latter may also be the case for the second inner and first inner heights 420', 410'.

Additionally, it can be seen that in 400" the third outer height 430", being the outer globally smallest height of the respective heights, is located in the lower back-facing part III: (rather than in the lower front-facing part II: as for the third inner height 430' of 400'). This is due to the radial or transverse slope of the contact surface (101) changing between increasing and decreasing across (near or at) a boundary between the lower back-facing part (104; III:) and the lower front-facing part (103, II:); see e.g. also FIG. 7. In other embodiments, this may be different. For the shown embodiment, the radial or transverse slope changes in the lower back-facing part III: from being generally negative or declining towards the inner opening and/or the centre or centre point of the cushion to being generally positively inclining towards the inner opening and/or centre or centre point of the cushion. This promotes an overall better fit to the head shape of user thereby increasing noise suppression and/or increasing user comfort.

In the shown and corresponding embodiments, the contact surface has a general negative or declining slope in radial or transverse directions towards the inner opening and/or the centre or centre point of the cushion at and near the first inner and outer heights 410', 410", at and near the second inner and outer heights 420', 420", and/or at and near the fourth inner and outer heights 440', 440" while the contact surface has a general positively inclined slope in radial or transverse directions towards the centre or centre point of the cushion. This also promotes an overall better fit to the head shape of user thereby increasing noise suppression and/or increasing user comfort.

In at least some embodiments and as can be seen from FIGS. 6a and *b* (see also FIGS. 6c and 7), the slopes at or near the second inner and outer heights 420', 420" (in part III:) is much greater than the slopes at or near the first inner and outer heights 410', 410" (in part I:).

As can be seen, the contact surface variation or the predetermined height profile of the cushion in the upper back-facing part IV: comprises, at least in the shown and corresponding embodiments, a non-monotonic segment.

In some non-rounded embodiments where the contact surface is radially sloped as disclosed herein, d1' is e.g. about 3 millimetres to about 8 millimetres, or more preferably about 4 millimetres to about 7 millimetres, e.g. about 6 millimetres, and d1" is e.g. about 7 millimetres to about 12 millimetres, more preferably about 8 millimetres to about 10 millimetres, e.g. about 9 millimetres. In some rounded embodiments, d1' is e.g. about 5 millimetres to about 10 millimetres, or more preferably about 6 millimetres to about 9 millimetres, e.g. about 7 millimetres, and d1" is e.g. about 6 millimetres to about 11 millimetres, more preferably about 7 millimetres to about 10 millimetres, e.g. about 9 millimetres.

In some non-rounded embodiments where the contact surface is radially sloped as disclosed herein, d2' is e.g. about 2 millimetres to about 7 millimetres, or more preferably about 3 millimetres to about 6 millimetres, e.g. about 4 millimetres, and d2" is e.g. about 7 millimetres to about 11 millimetres, or more preferably about 8 millimetres to about 10 millimetres, e.g. about 9 millimetres. In some rounded embodiments, d2' is e.g. about 4 millimetres to about 8 millimetres, or more preferably about 5 millimetres to about 7 millimetres, e.g. about 6 millimetres, and d2" is e.g. about 7 millimetres to about 11 millimetres, more preferably about 8 millimetres to about 10 millimetres, e.g. about 9 millimetres.

In some non-rounded embodiments where the contact surface is radially sloped as disclosed herein, d3' is e.g. about 1 millimetres to about 5 millimetres, or more preferably about 2 millimetres to about 4 millimetres, e.g. about 3 millimetres, and d3" is e.g. about 2 millimetres to about 6 millimetres, or more preferably about 3 millimetres to about 5 millimetres, e.g. about 4 millimetres. In some rounded embodiments, d3' is e.g. about 1 millimetres to about 6 millimetres, or more preferably about 2 millimetres to about 5 millimetres, e.g. about 3 millimetres, and d3" is e.g. about 2 millimetres to about 6 millimetres, or more preferably about 3 millimetres to about 5 millimetres, e.g. about 4 millimetres.

Figure 6C:
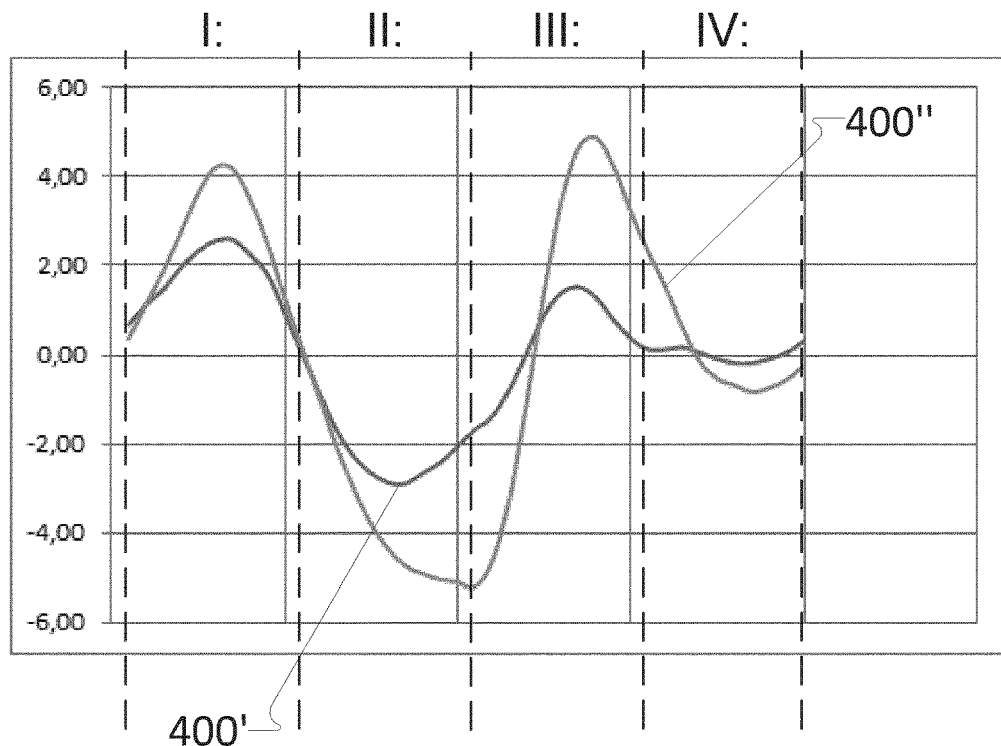

FIG. 6c schematically illustrates both the predetermined varying height profiles of FIGS. 6a and 6b together. Illustrated are the inner height profile 400' and the outer height profile 400" of FIGS. 6a and 6b of an embodiment of a radially or transversally sloped cushion. As readily can be seen from FIG. 6c, there are significant differences between the respective heights at the inner track 400' and the outer track 400' at some locations. In particular, at locations of the first height, the second height, and the third height. It can also be seen that the height difference between the inner track and outer track at the respective second inner and outer heights is greater compared e.g. to at the first heights indicating a greater radial slope at or near this location. At other (far fewer) locations, the difference between inner and outer height values is practically speaking non-existent. This is e.g. the case at/near the transition between the upper front-facing part (see e.g. I:/102 in FIG. 5a) 102/I: and the lower front-facing part (see e.g. 103/II: in FIG. 5a), near the peak associated with the second heights, and near a (inner) small peak being adjacent to the fourth height/the locally lowest valley. As mentioned, the close fit associated with such height profiles leads to increased noise suppression and user comfort. The difference in height values also leads to different radial/transverse slopes of the contact surface about the inner opening and/or centre or centre point, as e.g. is illustrated in FIG. 7 for the graphs of FIG. 6c. The radial or transverse width of the cushion (from inner to outer track/values) is an example about 20 millimetres.

FIG. 7 schematically illustrates varying radial slopes of a cushion according to one embodiment as obtained by registering slope values at measurements points. FIG. 7 schematically illustrates the varying radial or transversal slopes about the inner opening and/or the centre or centre point of a cushion where the slope is taken (as an example) from the inner height values (see e.g. 400' in FIGS. 6a and c) to the outer height values (see e.g. 400" in FIGS. 6b and c), i.e. an increase in height from an inner track to an outer track of the cushion will give a positive or increasing slope.

As readily can be seen from FIG. 7, the slopes vary substantially about the inner opening and/or the centre or centre point of the cushion indicating the fairly complex nature and shape of the cushion according to the associated sloped embodiment. Furthermore, it can be seen that slope changes sign (positive <-> negative) at four different locations roughly being near the beginning of segment or quadrant I:, near the beginning of segment or quadrant II:, near the middle of segment or quadrant III:, and near the middle of segment or quadrant IV:. Additionally, it can readily be seen that there generally are positive slopes in areas with peaks/maxima (i.e. near the first and second heights) and negative slopes in areas with valleys/minima (i.e. near the third and the fourth heights). Accordingly, it is readily further accommodated that the extent of recesses and the extent of bulges (e.g. due to the jaw) of a user's head generally increases with distance to the user's ear, leading to further increased noise suppression and user comfort by having the contact surface of a cushion more closely following also the radial extent of the recesses and bulges (even when the cushion is tilted).

Figure 8:
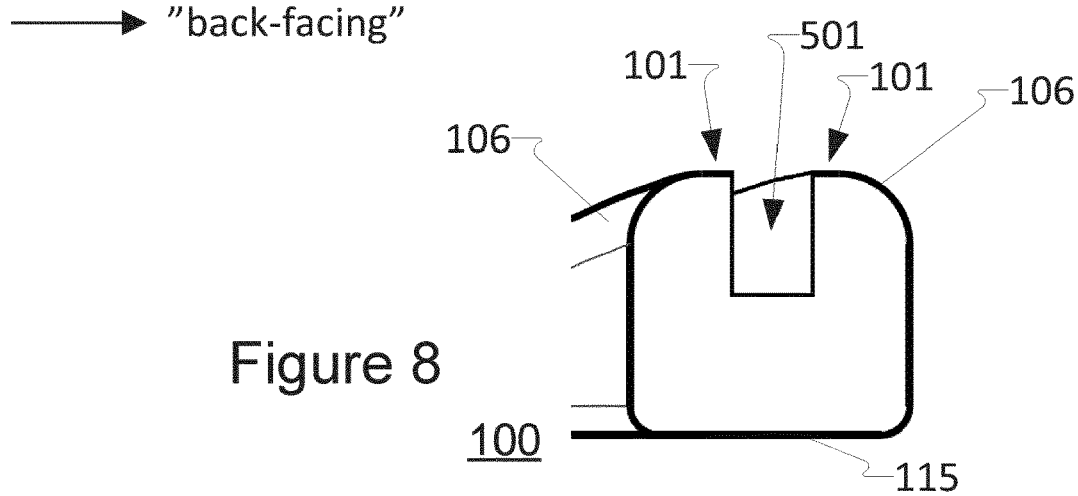
FIG. 8 schematically illustrates a cross-sectional view of a cushion according to alternative embodiments.

FIG. 8 schematically illustrates a cross-sectional view of a cushion according to alternative embodiments. Illustrated is a cross-sectional view of a rounded cushion 100 where there the cushion comprises a track, slit, groove, or the like 501 in the contact surface 101 of the cushion 100. The track, slit, groove, or the like 501 may e.g. be located centrally in the contact surface 101 in radial or transverse directions away from or towards the inner opening and/or the centre or centre point of the cushion. In at least some embodiments, the track, slit, groove, etc. 501 is located in the entire contact surface 101, i.e. all the way about the inner opening and/or the centre or centre point. Accordingly, the track, slit, groove, or the like 501 forms two ribs or the like in the cushion 100 with the proximal parts of the ribs forming the contact surface 101.

The cushion 100 may e.g. correspond to the ones illustrated in FIGS. 1, 3, 5a, 9, and 10 (as shown). Alternatively, the cushion 100 may e.g. be one where the contact surface 101 is radially sloped, at least at some locations, as disclosed herein and e.g. corresponding to the ones illustrated in FIGS. 2, 4, 5a, and 10.

FIGS. 9a-c schematically illustrates different views of a cushion according to alternative embodiments. Illustrated in FIGS. 9a-c is respectively a back view, a (right or front-facing) side view, and a perspective view of a cushion as disclosed herein where the cushion further comprises a number of alignment elements 801 provided protrudingly on the back, i.e. at the distal end or part, of the cushion 100. Further indicated are respective upper, lower, front-facing, and back-facing directions indicated in relation to FIG. 9a.

The alignment elements 801 are arranged in an asymmetrical pattern in relation to the upper and lower directions and/or the front-facing and back-facing directions so it is possible to distinguish the proper orientation of the cushion when it is to be inserted into or attached to an ear cup of a headset. The ear cup has a number of corresponding mating alignments elements (not shown) ensuring that the cushion 100 can only be inserted correctly into the ear cup when the respective alignment elements of the cushion 100 and the ear cup align and e.g. mate or connect. In the shown embodiment, the number of alignment elements 801 are two and the pattern is one where one element 801 (the shown uppermost element) is located centrally in the cushion 100 in relation to the front-facing and back-facing directions but offset in relation to the upper and lower directions and the other element 801 (the shown lowermost element) is located centrally in the cushion 100 in relation to the upper and lower directions but offset in relation to the front-facing and back-facing directions. The number of alignment elements 801 and/or the location pattern can be different for other embodiments.

In the shown and corresponding embodiments, the alignment elements 801 protrudes from the back side (distal side) of the cushion 100 and the ear cup comprises mating or accommodating openings. Alternatively, the ear cup could comprise protruding alignment elements and the cushion could comprise suitable openings. The alignment elements 801 may e.g. be made of a rigid material, e.g. plastic or similar.

Figure 10:
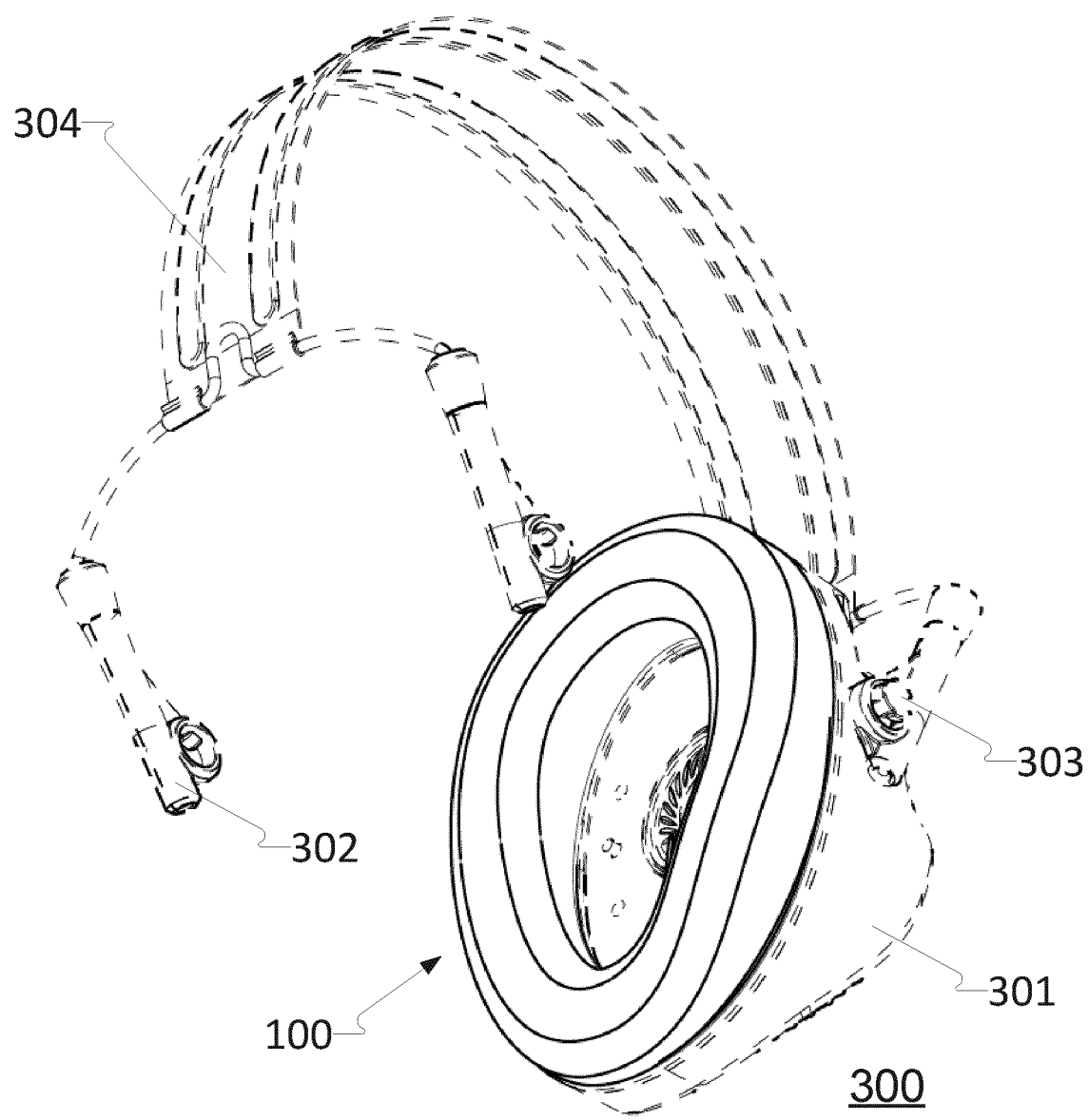
FIG. 10 schematically illustrates a headset and/or hearing protection device comprising a cushion as disclosed herein.

FIG. 10 schematically illustrates a headset and/or hearing protection device comprising a cushion as disclosed herein.

Illustrated is a headset and/or hearing protection device 300 comprising at least one ear cup 301, where at least one ear cup 301 comprises a cushion 100 as disclosed herein. The headset and/or hearing protection device 300 comprises, as an example, a headband or similar 304 having height adjustment elements 302 to which an ear cup 301 can be secured via a fixing element 303.

To better illustrate details, the headset and/or hearing protection device 300 is drawn with dashed lines and with only a single ear cup 301.

Some preferred embodiments have been shown in the foregoing, but it should be stressed that the invention is not limited to these, but may be embodied in other ways within the subject matter defined in the following claims.

It should be emphasized that the term "comprises/comprising" when used in this specification is taken to specify the presence of stated features, elements, steps or components but does not preclude the presence or addition of one or more other features, elements, steps, components or groups thereof.

In the claims enumerating several features, some or all of these features may be embodied by one and the same element, component or item. The mere fact that certain measures are recited in mutually different dependent claims or described in different embodiments does not indicate that a combination of these measures cannot be used to advantage.

In the claims, any reference signs placed between parentheses shall not be constructed as limiting the claim. The word "comprising" does not exclude the presence of elements or steps other than those listed in a claim. The word "a" or "an" preceding an element does not exclude the presence of a plurality of such elements.

The mere fact that certain measures are recited in mutually different dependent claims does not indicate that a combination of these measures cannot be used to an advantage.

It will be apparent to a person skilled in the art that the various embodiments of the invention as disclosed and/or elements thereof can be combined without departing from the scope of the invention as defined in the claims.

The invention claimed is:

1. A cushion configured to be secured to an ear cup of a headset and/or hearing protection device, wherein the cushion defines an inner opening and comprises
    a contact surface along a periphery proximal part of the cushion, the contact surface configured to abut against and contact a user's head around an ear of the user when the headset and/or hearing protection device is worn by the user,
    wherein
    the contact surface of the cushion has a predetermined height profile where respective height values of the predetermined height profile at a plurality of locations of the contact surface vary about the inner opening and/or a centre or centre point of the cushion,
    a first height of the predetermined height profile is a globally largest height of the respective height values at the plurality of locations, where the plurality of locations is located at least nearest or towards and about the inner opening and/or the centre or centre point and where the first height is located in an upper front-facing part of the cushion, and
    wherein the contact surface is a generally flat surface in radial or transverse directions away from or towards the inner opening and/or the centre or centre point of the cushion.

2. The cushion according to claim 1, wherein a second height of the predetermined height profile is a locally largest height of the respective height values at the plurality of locations where the second height is located in a lower back-facing part of the cushion.

3. The cushion according to claim 1, wherein a third height of the predetermined height profile is a globally smallest height of the respective height values where the third height is located in a lower part of the cushion, or in a lower front-facing part of the cushion, or in a lower back-facing part of the cushion.

4. The cushion according to claim 1, wherein a fourth height of the predetermined height profile is a locally smallest height of the respective height values where the fourth height is located in a back-facing part of the cushion or in an upper back-facing part of the cushion.

5. The cushion according to claim 4, wherein the fourth height is located in an upper back-facing part of the cushion and wherein the respective height values of the predetermined height profile in the upper back-facing part includes at least a non-monotonic segment.

6. The cushion according to claim 1, wherein
    a first difference in height between the first height and the third height is about 4 millimetres to about 10 millimetres, or about 6 millimetres to about 8 millimetres, or about 7 millimetres, and/or wherein
    a second difference in height between the second height and the third height is about 3 millimetres to about 9 millimetres, or about 5 millimetres to about 7 millimetres, or about 6 millimetres, and
    the second difference in height is smaller than the first difference in height,
    and/or wherein
    a third difference in height between the fourth height and the third height is about 1 millimetres to about 6 millimetres, or about 2 millimetres to about 4 millimetres, or about 3 millimetres, and
    the third difference in height is smaller than the first difference in height, and, if the cushion comprises a second height, the third difference in height is furthermore smaller than the second difference in height.

7. The cushion according to claim 1, wherein
    a second difference in height between the second height and the third height is about 70% to about 90%, or about 75% to about 85%, or about 78% to about 82%, or about 80%, of a first difference in height between the first height and the third height, and/or
    a third difference in height between the fourth height and the third height is about 35% to about 60%, or about 40% to about 55%, or about 45% to about 50%, or about 47%, of a first difference in height between the first height and the third height.

8. The cushion according to claim 1, wherein the overall shape of the cushion as seen in the proximal, or in the distal direction, is generally oval and/or the cushion is integrally formed.

9. The cushion according to claim 1, wherein the cushion comprises a central, or radially offset, track, slit, or groove in the contact surface about the centre or centre point.

10. The cushion according to claim 1, wherein the cushion comprises a number of alignment elements arranged on a distal side of the cushion in a predetermined pattern, where the predetermined pattern is asymmetrical in relation to upper and lower directions and/or to front-facing and back-facing directions of the cushion, where the alignment elements are
    configured to mate or fit with a number of corresponding alignment elements of an ear cup of a headset and/or hearing protection device that the cushion is to be fitted to.

11. A headset and/or a hearing protection device comprising one or two ear cups, wherein at least one ear cup comprises a cushion according to claim 1.

12. A cushion configured to be secured to an ear cup of a headset and/or hearing protection device, wherein the cushion defines an inner opening and comprises a contact surface along a periphery proximal part of the cushion, the contact surface configured to abut against and contact a user's head around an ear of the user when the headset and/or hearing protection device is worn by the user, wherein the contact surface of the cushion has a predetermined height profile where respective height values of the predetermined height profile at a plurality of locations of the contact surface vary about the inner opening and/or a centre or centre point of the cushion, a first height of the predetermined height profile is a globally largest height of the respective height values at the plurality of locations, where the plurality of locations is located at least nearest or towards and about the inner opening and/or the centre or centre point and where the first height is located in an upper front-facing part of the cushion, and wherein the contact surface has varying slopes, at least at some locations, in radial or transverse directions away from or towards the inner opening and/or the centre or centre point of the cushion.

13. The cushion according to claim 12, wherein a second height of the predetermined height profile is a locally largest height of the respective height values at the plurality of locations where the second height is located in a lower back-facing part of the cushion.

14. The cushion according to claim 12, wherein a third height of the predetermined height profile is a globally smallest height of the respective height values where the third height is located in a lower part of the cushion, or in a lower front-facing part of the cushion, or in a lower back-facing part of the cushion.

15. The cushion according to claim 12, wherein a fourth height of the predetermined height profile is a locally smallest height of the respective height values where the fourth height is located in a back-facing part of the cushion or in an upper back-facing part of the cushion.

16. The cushion according to claim 15, wherein the fourth height is located in an upper back-facing part of the cushion and wherein the respective height values of the predetermined height profile in the upper back-facing part includes at least a non-monotonic segment.

17. The cushion according to claim 12, wherein the predetermined height profile comprises a first inner height and a first outer height and where a third inner height of the predetermined height profile is a globally smallest inner height of the respective height values and where a third outer height of the predetermined height profile is a globally smallest outer height of the respective height values, where the third inner and outer heights are located in a lower part of the cushion, or in a lower front-facing part of the cushion or in a lower back-facing part.

18. The cushion according to claim 17, wherein
a first inner difference in height between the first inner height and the third inner height is about 3 millimetres to about 8 millimetres, or
about 4 millimetres to about 7 millimetres or about 6 millimetres, and/or
a first outer difference in height between the first outer height and the third outer height is about 7 millimetres to about 12 millimetres, or about 8 millimetres to about 11 millimetres, or about 9 millimetres, or about 9.4 millimetres.

19. The cushion according to claim 12, wherein
a second inner height of the predetermined height profile is a locally largest inner height of the respective height values, where the second inner height is located in a lower back-facing part of the cushion, and
a second outer height of the predetermined height profile is a locally largest outer height of the respective height values or a globally largest outer height of the respective height values, where the second outer height is located in a lower back-facing part.

20. The cushion according to claim 19, wherein
a second inner difference in height between the second inner height and the third inner height is about 2 millimetres to about 7 millimetres, or about 3 millimetres to about 6 millimetres, or about 4 millimetres, and/or
a second outer difference in height between the second outer height and the third outer height is about 7 millimetres to about 11 millimetres, or about 8 millimetres to about 10 millimetres, or about 9 millimetres, and
wherein the second inner difference in height is smaller than the first inner difference in height.

21. The cushion according to claim 12, wherein a fourth inner height of the predetermined height profile is a locally smallest inner height of the respective height values, and a fourth outer height of the predetermined height profile is a locally smallest outer height of the respective height values, and where the fourth inner and outer heights are located in a back-facing part of the cushion, or in an upper back-facing part of the cushion.

22. The cushion according to claim 21, wherein
a third inner difference in height between the fourth inner height and the third inner height is about 1 millimetres to about 5 millimetres, or about 2 millimetres to about 4 millimetres, or about 3 millimetres, and/or
a third outer difference in height between the fourth outer height and the third outer height is about 2 millimetres to about 6 millimetres, or about 3 millimetres to about 5 millimetres, or about 4 millimetres, and
wherein the third inner difference in height is smaller than the first inner difference in height, and/or wherein the third outer difference in height is smaller than the first outer difference in height, and if the cushion comprises a second height, the third inner difference in height is smaller than the second inner difference in height and/or the third outer difference in height is smaller than the second outer difference in height.

23. The cushion according to claim 12, wherein
a second inner difference in height between the second inner height and the third inner height is about 75% to about 95%, or about 80% to about 90%, or about 75% to about 85%, or about 80%, of a first inner difference in height between the first inner height and the third inner height, and/or
wherein a third inner difference in height between the fourth inner height and the third inner height is about 35% to about 65%, or about 40% to about 60%, or about 45% to about 55%, or about 50%, of a first inner difference in height between the first inner height and the third inner height.

24. The cushion according to claim 12, wherein
the second outer difference in height between the second outer height and the third outer height is about 100% to about 115%, or about 105% to about 110%, or about 107%, of a first outer difference in height between the first outer height and the third outer height, and/or
wherein the third outer difference in height between the fourth outer height and the third outer height is about 35% to about 60%, or about 40% to about 55%, or about 45% to about 50%, or about 47%, of a first outer difference in height between the first outer height and the third outer height.

25. The cushion according to claim 16, wherein the contact surface has generally positive slopes in radial or transverse directions away from the inner opening and/or the centre or centre point of the cushion at or near the first height and/or at or near the second height, and wherein the contact surface has generally negative or declining slopes in radial or transverse directions away from the inner opening and/or the centre or centre point of the cushion at or near the third height and/or at or near the fourth height.

26. The cushion according to claim 12, wherein the varying slopes of the contact surface in radial or transverse directions away from the inner opening and/or the centre or centre point of the cushion has a global minimum value near or at a boundary between the lower back-facing part and the lower front-facing part.

27. The cushion according to claim 12, wherein the overall shape of the cushion as seen in the proximal, or in the distal direction, is generally oval and/or the cushion is integrally formed.

28. The cushion according to claim 12, wherein the cushion comprises a central, or radially offset, track, slit, or groove in the contact surface about the centre or centre point.

29. The cushion according to claim 12, wherein the cushion comprises a number of alignment elements arranged on a distal side of the cushion in a predetermined pattern, where the predetermined pattern is asymmetrical in relation to upper and lower directions and/or to front-facing and back-facing directions of the cushion, where the alignment elements are
   configured to mate or fit with a number of corresponding alignment elements of an ear cup of a headset and/or hearing protection device that the cushion is to be fitted to.

30. A headset and/or a hearing protection device comprising one or two ear cups, wherein at least one ear cup comprises a cushion according to claim 12.

* * * * *